United States Patent
Glover et al.

(10) Patent No.: US 11,197,619 B2
(45) Date of Patent: *Dec. 14, 2021

(54) SYSTEM AND APPARATUS COMPRISING A MULTI-SENSOR CATHETER FOR RIGHT HEART AND PULMONARY ARTERY CATHETERIZATION

(71) Applicant: Three Rivers Cardiovascular Systems Inc., Toronto (CA)

(72) Inventors: Christopher Glover, Toronto (CA); Eric Caron, Toronto (CA); Sylvain Abel, Shawinigan (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/587,659

(22) Filed: Sep. 30, 2019

(65) Prior Publication Data
US 2020/0046234 A1 Feb. 13, 2020

Related U.S. Application Data

(63) Continuation of application No. 15/293,380, filed on Oct. 14, 2016, now Pat. No. 10,463,259, which is a
(Continued)

(51) Int. Cl.
*A61B 5/0215* (2006.01)
*A61B 5/00* (2006.01)
(Continued)

(52) U.S. Cl.
CPC ............ *A61B 5/02154* (2013.01); *A61B 5/01* (2013.01); *A61B 5/026* (2013.01); *A61B 5/028* (2013.01);
(Continued)

(58) Field of Classification Search
CPC . A61B 5/02154; A61B 5/0295; A61B 5/0261; A61B 5/02055; A61B 5/026;
(Continued)

(56) References Cited

U.S. PATENT DOCUMENTS

| 4,543,961 A | 10/1985 | Brown |
| 4,621,929 A | 11/1986 | Philips |

(Continued)

FOREIGN PATENT DOCUMENTS

| CN | 102202562 | 9/2011 |
| EP | 1105181 | 6/2001 |

(Continued)

OTHER PUBLICATIONS

Pinet et al.; "Ultra-miniature all-glass Fabry-Perot pressure sensor manufactured at the tip of a multimode optical fiber"; FISO Technologies Inc.; Proceedings of SPIE, vol. 6770 (2007).
(Continued)

*Primary Examiner* — Gary Jackson
*Assistant Examiner* — Sebastian X Lukjan
(74) *Attorney, Agent, or Firm* — Miltons IP/p.i.

(57) ABSTRACT

A system and apparatus comprising a multi-sensor catheter for right heart and pulmonary artery catheterization is disclosed. The multi-sensor catheter comprises multi-lumen catheter tubing into which at least three optical pressure sensors, and their respective optical fibers, are inserted. The three optical pressure sensors are arranged within a distal end portion of the catheter, spaced apart lengthwise within the distal end portion for measuring pressure concurrently at each sensor location. The sensor locations are configured for placement of at least one sensor in each of the right atrium, the right ventricle and the pulmonary artery, for concurrent measurement of pressure at each sensor location. The sensor arrangement may further comprise an optical thermo-dilution sensor, and another lumen is provided for fluid injection for thermo-dilution measurements. The catheter may comprise an inflatable balloon tip and a guidewire lumen, and preferably has an outside diameter of 6 French or less.

7 Claims, 13 Drawing Sheets

Related U.S. Application Data continuation-in-part of application No. 14/874,604, filed on Oct. 5, 2015, now Pat. No. 9,504,392, which is a continuation of application No. 14/354,624, filed as application No. PCT/IB2012/055893 on Oct. 26, 2012, now Pat. No. 9,149,230.

(60) Provisional application No. 61/552,778, filed on Oct. 28, 2011, provisional application No. 61/552,787, filed on Oct. 28, 2011.

(51) Int. Cl.

| | | |
|---|---|---|
| *A61B 5/028* | (2006.01) | |
| *A61F 2/24* | (2006.01) | |
| *A61M 25/10* | (2013.01) | |
| *A61B 5/0295* | (2006.01) | |
| *A61B 5/026* | (2006.01) | |
| *G01P 5/10* | (2006.01) | |
| *A61B 5/0205* | (2006.01) | |
| *G01K 11/32* | (2021.01) | |
| *G01K 13/02* | (2021.01) | |
| *A61B 5/01* | (2006.01) | |
| *G01L 11/02* | (2006.01) | |
| *G16H 20/40* | (2018.01) | |
| *A61B 90/00* | (2016.01) | |
| *A61B 90/30* | (2016.01) | |
| *G16H 40/63* | (2018.01) | |
| *A61B 5/024* | (2006.01) | |

(52) U.S. Cl.
CPC ........ *A61B 5/0215* (2013.01); *A61B 5/02055* (2013.01); *A61B 5/0261* (2013.01); *A61B 5/0295* (2013.01); *A61B 5/02158* (2013.01); *A61B 5/6851* (2013.01); *A61B 5/6852* (2013.01); *A61B 5/6853* (2013.01); *A61B 5/743* (2013.01); *A61B 5/7425* (2013.01); *A61F 2/2427* (2013.01); *A61M 25/1018* (2013.01); *A61M 25/1025* (2013.01); *G01K 11/32* (2013.01); *G01K 13/02* (2013.01); *G01L 11/02* (2013.01); *G01P 5/10* (2013.01); *G16H 20/40* (2018.01); *A61B 5/0002* (2013.01); *A61B 5/024* (2013.01); *A61B 2090/306* (2016.02); *A61B 2090/3966* (2016.02); *A61B 2562/028* (2013.01); *A61B 2562/0233* (2013.01); *A61B 2562/0247* (2013.01); *A61B 2562/0266* (2013.01); *A61B 2562/04* (2013.01); *A61M 2025/1079* (2013.01); *G16H 40/63* (2018.01)

(58) Field of Classification Search
CPC ......... A61B 5/743; A61B 5/0215; A61B 5/01; A61B 5/7425; A61B 5/02158; A61B 5/6851; A61B 5/6853; A61B 5/028; A61B 5/0002; A61B 5/024; A61B 2090/3966; A61B 2562/0233; A61B 2562/0247; A61B 2562/0266; A61B 2090/306; A61B 2562/04; A61B 2562/028; A61B 5/4836; A61B 5/6852; G16H 20/40; G16H 40/63; G01P 5/10; G01K 11/32; G01K 13/02; G01L 11/02; A61F 2/2427; A61M 25/1018; A61M 25/1025; A61M 2025/1079

See application file for complete search history.

(56) References Cited

U.S. PATENT DOCUMENTS

| | | |
|---|---|---|
| 4,730,622 A | 3/1988 | Cohen |
| 4,735,212 A | 4/1988 | Cohen |
| 4,850,358 A | 7/1989 | Millar |
| 4,873,989 A | 10/1989 | Einzig |
| 4,901,731 A | 2/1990 | Millar |
| 4,953,553 A | 9/1990 | Tremulis |
| 4,966,148 A | 10/1990 | Millar |
| 5,006,119 A | 4/1991 | Acker |
| 5,018,529 A | 5/1991 | Tenerz et al. |
| 5,115,127 A | 5/1992 | Bobb |
| 5,125,058 A | 6/1992 | Tenerz et al. |
| 5,152,291 A | 10/1992 | Dias |
| 5,178,153 A | 1/1993 | Einzig |
| 5,208,650 A | 5/1993 | Giallorenzi |
| 5,226,423 A | 7/1993 | Tenerz et al. |
| 5,392,117 A | 2/1995 | Belleville et al. |
| 5,514,128 A | 5/1996 | Hillsman et al. |
| 5,520,190 A | 5/1996 | Benedict et al. |
| 5,574,699 A | 11/1996 | Cuomo |
| 5,873,835 A | 2/1999 | Hastings et al. |
| 6,107,004 A | 8/2000 | Donadio, III |
| 6,112,598 A | 9/2000 | Tenerz et al. |
| 6,167,763 B1 | 1/2001 | Tenerz et al. |
| 6,254,550 B1 | 7/2001 | McNamara et al. |
| 6,336,906 B1 | 1/2002 | Hammarstrom et al. |
| 6,343,514 B1 | 2/2002 | Smith |
| 6,431,010 B1 | 8/2002 | Joffe |
| 6,585,660 B2 | 7/2003 | Dorando et al. |
| 6,615,667 B2 | 9/2003 | Smith |
| 6,976,965 B2 | 12/2005 | Corl et al. |
| 6,986,739 B2 | 1/2006 | Warren et al. |
| 7,097,620 B2 | 8/2006 | Corl et al. |
| 7,134,994 B2 | 11/2006 | Alpert et al. |
| 7,274,956 B2 | 9/2007 | Mott et al. |
| 7,329,223 B1 | 2/2008 | Ainsworth et al. |
| 7,450,989 B2 | 11/2008 | Svanerudh |
| 7,532,920 B1 | 5/2009 | Ainsworth et al. |
| 7,684,657 B2 | 3/2010 | Donlagic |
| 7,689,071 B2 | 3/2010 | Belleville et al. |
| 7,731,664 B1 | 6/2010 | Millar |
| 7,783,338 B2 | 8/2010 | Ainsworth et al. |
| 7,931,603 B2 | 4/2011 | Von Malmborg et al. |
| 7,967,761 B2 | 6/2011 | Smith |
| 7,967,762 B2 | 6/2011 | Corl et al. |
| 8,317,715 B2 | 11/2012 | Belleville et al. |
| 8,758,333 B2 | 6/2014 | Harlan |
| 8,936,401 B2 | 1/2015 | Belleville |
| 9,052,466 B2 | 6/2015 | Belleville et al. |
| 9,149,230 B2 | 10/2015 | Caron |
| 10,463,259 B2* | 11/2019 | Glover ............... A61B 5/02055 |
| 2003/0095263 A1 | 5/2003 | Varshneya et al. |
| 2003/0100824 A1 | 5/2003 | Warren et al. |
| 2004/0075841 A1 | 4/2004 | Van Neste et al. |
| 2004/0253365 A1 | 12/2004 | Warren et al. |
| 2006/0133715 A1 | 6/2006 | Belleville et al. |
| 2007/0038173 A1 | 2/2007 | Simpson |
| 2008/0249388 A1 | 10/2008 | Kumhyr |
| 2008/0312597 A1 | 12/2008 | Uihlein |
| 2010/0228112 A1 | 9/2010 | Von Malmborg |
| 2010/0234698 A1* | 9/2010 | Manstrom ............ A61B 5/0002 600/301 |
| 2010/0241008 A1 | 9/2010 | Belleville et al. |
| 2011/0004198 A1 | 1/2011 | Hoch |
| 2011/0023617 A1 | 2/2011 | Yu et al. |
| 2011/0066047 A1 | 3/2011 | Belleville et al. |
| 2011/0092784 A1 | 4/2011 | Butler et al. |
| 2011/0234698 A1 | 9/2011 | Sakata et al. |
| 2012/0197097 A1 | 8/2012 | Chan |
| 2012/0227505 A1 | 9/2012 | Belleville et al. |
| 2013/0051731 A1 | 2/2013 | Belleville et al. |
| 2013/0218032 A1 | 8/2013 | Belleville |
| 2013/0317372 A1 | 11/2013 | Eberle et al. |
| 2014/0039325 A1 | 2/2014 | Belleville |
| 2014/0107624 A1 | 4/2014 | Belleville |
| 2014/0241669 A1 | 8/2014 | Belleville et al. |

(56) References Cited

U.S. PATENT DOCUMENTS

| | | | |
|---|---|---|---|
| 2014/0243688 A1 | 8/2014 | Caron et al. | |
| 2014/0248021 A1 | 9/2014 | Belleville et al. | |
| 2014/0249386 A1 | 9/2014 | Caron et al. | |
| 2015/0057532 A1 | 2/2015 | Belleville | |
| 2016/0022159 A1 | 1/2016 | Caron et al. | |
| 2020/0022587 A1* | 1/2020 | Glover | A61B 5/4255 |

FOREIGN PATENT DOCUMENTS

| | | | |
|---|---|---|---|
| EP | 1849409 | 10/2007 | |
| JP | H05329119 | 12/1993 | |
| JP | 2003507111 | 2/2003 | |
| JP | 2005291945 | 10/2005 | |
| JP | 2007296354 | 11/2007 | |
| WO | 0113789 | 3/2001 | |
| WO | 2011048509 | 4/2011 | |
| WO | WO-2011048509 A1 * | 4/2011 | A61B 1/005 |
| WO | 2011101813 | 8/2011 | |
| WO | 2012061935 | 5/2012 | |
| WO | 2012164481 | 12/2012 | |
| WO | WO-2015054296 A1 * | 4/2015 | A61B 5/6851 |
| WO | 2015142623 | 9/2015 | |
| WO | 2016009317 | 1/2016 | |

OTHER PUBLICATIONS

Hamel et al.; "Temperature and pressure Fiber-Optic sensors applied to minimally invasive diagnostics and therapies"; FISO Technologies Inc.; Whitepaper/Publication; (2006).
Pinet, Eric; "Pressure measurement with fiber-optic sensors; Commercial technologies and applications"; FISO Technologies Inc.; 21st International Conference on Optical Fiber Sensors, edited by Wojtek J. Bock et al.; Proc. of SPIE vol. 7753 (May 17, 2011).
Pinet, Eric; "Disposable fiber-optic sensors for clinical environments"; SPIE 2007.
Tenerz, L.; "A Fiberoptic Silicon Pressure Microsensor for Measurements in Coronary Arteries"; Radi Medical Systems; IEEE 1991.
Hamel et al.; "Pressure Fiber-Optic Sensors in Intra-aortic Balloon Pumping Therapy"; European Medical Device Manufacturer Editorial: Sensors and Transducers integrated in medical equipment or used in manufacturing process; FISO Technologies Inc.; Whitepaper/Publication; (2006).
FOP-F125 Pressure Sensor; FISO Technologies Inc.; Preliminary Datasheet dated 2008.
PressureWire Certus FFR Measurement System; Product information dated 2011 and 2009.
PressureWire Certus FFR Measurement System; Product information; 2011.
Vaguine et al.; "Multiple Sensor Optical Thermometry System for Application in Clinical Hyperthermia" IEEE Transactions on Biomedical Engineering vol. BME-31, No. 1, pp. 168-172; Jan. 1984.
Silvestri et al.; Optical fiber measurement systems for medical applications; p. 205-225; Oct. 5, 2011.
Chinese Office Action (with English Translation) issue on CN Application No. 201280059712.X; dated Nov. 3, 2015; 14 pages.
Harrison, G. J. et al.; Experimental Investigation; "Guidewire Stiffness: What's in a Name?" J. Endovasc. Ther. 2011:18, pp. 797-801.
St. Jude Medical—Product Literature: PressureWire Certus FFR Measurement System; 2011; 5 pages.
JPO Machine translation of JP2005-291945.
JPO Machine translation of JPH05-329119.
Jeremy Fernando, "Pulmonary Artery Catheters", updated Dec. 22, 2014 (http://lifeinthefastlane.com/ccc/pulmonary-artery-catheters/); pp. 1-7.
"Swan-Ganz—right heart catheterization", NIH National Library of Medicine, online Medical Encyclopedia, Update Date Aug. 12, 2014 (https://www.nlm.nih.gov/medlineplus/ency/article/003870.htm); 4 pages.
"Pulmonary artery catheter", Wikipedia, version last modified May 8, 2016 (https://en.wikipedia.org/wiki/Pulmonary_artery_catheter); pp. 1-5.
Jan M. Headley, RN, BS, CCRN; "Invasive Hemodynamic Monitoring: Physiological Principles and Clinical Applications"; Edwards Life Sciences; Irvine, California, © 2002 (http://ht.edwards.com/resourcegallery/products/swanganz/pdfs/invasivehdmphysprincbook.pdf ); 40 pages.
B. Paunovic et al., "Pulmonary Artery Catheterization", (c) 2011, updated Jan. 3, 2016 (http://emedicine.medscape.com/article/1824547 (c) 2011); 10 pages.
"Right Heart Catheterization", Johns Hopkins Medicine Health Library, version downloaded Aug. 2016 (http://www.hopkinsmedicine.org/healthlibrary/test_procedures/cardiovascular/right_heart_catheterization_135,40/ ); 7 pages.
M. Kern, "Comparing FFR Tools New wires Pressure Microcatheter", Cath Lab Digest, vol. 24, Issue 5, May 2016 (http://www.cathlabdigest.com/article/Comparing-FFR-Tools-New-Wires-Pressure-Microcatheter); 4 pages.
De Vecchi et al., "Catheter induced Errors in Pressure Measurements in Vessels: An in-vitro and numerical study" IEEE Transactions on Biomedical Engineering, vol. 61, No. 6, Jun. 2014; pp. 1844-1850.
Robert G. Gray et al., "Feasibility of In Vivo Pressure Measurement using a pressure tip catheter via transventricular puncture", ASAIO J. 2010 56(3) 194-199; May 1, 2011; pp. 1-14.
Eric Pinet, et al., FISO Technologies, "Temperature fiber-optic point sensors: Commercial technologies and industrial applications", MIDEM Conference Proceedings, Sep. 29-Oct. 1, 2010, Radenci, Slovenia, D. Đonlagić, I. Šorli, & P. Šorli (Eds), MIDEM (Pub.) ISBN 978-961-92933-0-0; pp. 31-43.
Boston Scientific—Comet(TM) FR Guidewire—Product Literature—Oct. 2015; 2 pages.
Volcano Prime Wire Prestige—Product literature—Nov. 2012; 1 page.
Javier Escaned, "Boston Scientific: Designing the pressure guidewire for contemporary PCI scenarios", European Heart House, Coronary Physiology in the Catheterization Laboratory (9th Edition) Thursday Apr. 23-Saturday Apr. 25, 2015; 15 pages.
Opsens Medical, Product Brochure "One Wire. Many possibilities" Opto Wire One, www.opsensmedical.com, 2014 Brochure; 5 pages.
Webb, et al., "Current Status of Transcatheter Aortic Valve Replacement", Journal of the American College of Cardiology, vol. 60, No. 6, 2012; pp. 483-492.
Roy, D. A. et al., "First-in-man assessment of a dedicated guidewire for transcatheter aortic valve implantation", EuroIntervention 2013, 8, pp. 1019-1025.
Volcano Prime Wire Prestige—Product Literature: Jan. 2015 and Feb. 2015; 3 pages.
St. Jude Medical—PressureWire Aeris; Agile Tip Technology; "Wireless FFR Measurement with Outstanding Handling Performance" Product Literature; 2013; 2 pages.

* cited by examiner

A-A CUT-THROUGH VIEW OF FIGS. 5, 6 AND 9

B-B CUT-THROUGH VIEW OF FIG. 6

A-A CUT-THROUGH VIEW OF FIG. 10

B-B CUT-THROUGH VIEW OF FIG. 10

SYSTEM AND APPARATUS COMPRISING A MULTI-SENSOR CATHETER FOR RIGHT HEART AND PULMONARY ARTERY CATHETERIZATION

CROSS-REFERENCE TO RELATED APPLICATIONS

This application is continuation of U.S. patent application Ser. No. 15/293,380 filed Oct. 14, 2016, which is a Continuation-in-Part of U.S. patent application Ser. No. 14/874,604, filed Oct. 5, 2015, which is a Continuation of U.S. patent application Ser. No. 14/354,624, filed Apr. 28, 2014, which is a national stage entry of PCT International Application No. PCT/IB2012/055893, entitled "Apparatus, system and methods for measuring a blood pressure gradient", filed Oct. 26, 2012, which claims priority from U.S. Provisional patent application No. 61/552,778 entitled "Apparatus, system and methods for measuring a blood pressure gradient", filed Oct. 28, 2011 and from U.S. Provisional patent application No. 61/552,787 entitled "Fluid temperature and flow sensor apparatus and system for cardiovascular and other medical applications", filed Oct. 28, 2011; all these applications are incorporated herein by reference, in their entirety.

This application is a related to U.S. patent application Ser. No. 15/001,347, filed Jan. 20, 2016, entitled "System and Apparatus Comprising a Multisensor Guidewire for Use in Interventional Cardiology", which is a Continuation-in-Part of PCT International Application No. PCT/IB2015/055240, of the same title, filed Jul. 10, 2015, designating the United States, and claiming priority from U.S. Provisional patent application No. 62/023,891, entitled "System And Apparatus Comprising a Multisensor Support Guidewire for Use in Trans-Catheter Heart Valve Therapies", filed Jul. 13, 2014 and from U.S. Provisional patent application No. 62/039,952, entitled "System And Apparatus Comprising a Multisensor Support Guidewire for Use in Trans-Catheter Heart Valve Therapies", filed Aug. 21, 2014; all said applications are incorporated herein by reference in their entirety.

TECHNICAL FIELD

The present invention relates to a system and apparatus comprising a multi-sensor catheter or a multi-sensor guidewire for use in cardiology, and more particularly to a pulmonary artery catheter for right heart catheterization and related diagnostic measurements.

BACKGROUND

The above referenced related patent applications disclose multi-sensor guidewires and multi-sensor micro-catheters for use in interventional cardiology. For example, if a heart valve is found to be malfunctioning because it is defective or diseased, minimally invasive methods are known for repair and replacement of the heart valve, by introduction of a catheter intravascularly into the heart to access the heart valve. Percutaneous procedures for minimally invasive transcatheter heart valve diagnosis, repair and replacement avoid the need for open heart surgery. These procedures may be referred to as Transcatheter Valve Therapies (TVT).

TVT for valve repair include, for example, procedures such as, balloon valvuloplasty to widen an aortic valve which is narrowed by stenosis, or insertion of a mitral clip to reduce regurgitation when a mitral valve fails to close properly. Alternatively, if the valve cannot be repaired, a prosthetic replacement valve may be introduced. Minimally invasive Transcatheter heart Valve Replacement (TVR) procedures, including Transcatheter Aortic Valve Implantation (TAVI or TAVR) and Transcatheter Mitral Valve Implantation (TMVI), have been developed over the last decade and have become more common procedures in recent years.

While there have been many recent advances in systems and apparatus for TVT and for related diagnostic procedures, interventional cardiologists who perform these procedures have identified the need for improved apparatus for use in TVT, including apparatus for heart valve replacement. They are also seeking improved diagnostic equipment that provides real-time direct measurements, i.e. within the heart, of important hemodynamic cardiovascular parameters before, during and after TVT.

The above referenced related U.S. patent application Ser. Nos. 14/874,604 and 14/354,624 (now issued to U.S. Pat. No. 9,149,230) having common inventorship and ownership with the present application, disclose a multi-sensor micro-catheter and a multi-sensor guidewire. These multi-sensor micro-catheters and guidewires comprise a distal end portion containing multiple optical sensors arranged for measuring blood pressure at several sensor locations, simultaneously, in real-time. Optionally, they include an optical or electrical sensor for measuring blood flow. The disclosed multi-sensor micro-catheters and multi-sensor guidewires can be configured for use in minimally invasive surgical procedures for measurement of intra-vascular pressure gradients, and more particularly, for direct measurement of a transvalvular pressure gradient within the heart, for any one of the four heart valves.

For example, a transvalvular measurement of pressure across the aortic valve, i.e. with pressure sensors positioned to measure pressure concurrently in the ascending aorta and left ventricle, allows for assessment of aortic regurgitation, before and after a TAVI procedure.

A need for improved diagnostic apparatus for right heart catheterization (RHC) and pulmonary artery (PA) catheterization has also been identified. For example, RHC may be performed in an Intensive Care Unit (ICU) for monitoring of critically ill patients. In a Cardiac Catheterization Lab (Cath Lab), RHC may be used for monitoring and diagnosis, and in the operating room (OR) for monitoring of important hemodynamic parameters during cardiac surgery or other high risk surgery.

During RHC and PA catheterization, a special balloon tipped catheter, which may be referred to as a pulmonary artery catheter (PA catheter) or a Swan Ganz (SG) catheter, is introduced through one of the larger veins, e.g. through an internal jugular vein, subclavian vein in the neck, or a median cubital vein in the arm, into the superior vena cava, or through a femoral vein into the inferior vena cava. The catheter tip is then introduced from the vena cava into the right atrium of the heart, advanced through the tricuspid valve into the right ventricle, and then through the pulmonic valve (alternatively called the pulmonary valve) into the PA, which is the main artery that carries de-oxygenated blood from the heart to the lungs. One lumen of the PA catheter extends from the proximal end to an opening at the distal tip. This lumen is fluid filled and is connected at its proximal end to an externally placed pressure transducer to enable the pressure at the distal tip to be monitored. Thus the pressure at the distal tip may be monitored by the catheter as it is advanced sequentially, firstly into the right atrium (RA), secondly into the right ventricle (RV) and thirdly into the PA. During these measurements the balloon may be partially inflated to allow the balloon to "float" and be drawn into the PA by the blood flow. Subsequently, after further inflating the balloon, the balloon is drawn by the blood flow and wedges in a smaller pulmonary blood vessel for measurement of a Pulmonary Capillary Wedge Pressure (PCWP). PCWP is an indirect measure of the left atrial pressure (LAP) and left ventricular end-diastolic pressure (LVEDP). At each point a characteristic pressure waveform is observed, and pressure measurements are recorded. That is, as the catheter tip is advanced, the observed waveform will change sequentially and show the transition from a RA pressure waveform, a RV pressure waveform, a PA pressure waveform and then a PCWP waveform.

Conventional four lumen/four port PA/SG catheters provide: one lumen for pressure monitoring at the catheter tip using an externally connected pressure transducer; a balloon inflation lumen; a thermistor lumen; and a fluid injection lumen for measurement of blood flow by thermo-dilution. The port for the pressure transducer may also be used for blood sampling, e.g. for measurement of mixed venous oxygen saturation ($SvO_2$). Some available PA catheters include two pressure sensing lumens, which can be connected to two external pressure transducers for measurement of pressures in the right atrium and in the pulmonary artery. Advanced PA catheters or SG catheters may also include several additional lumens and ports, e.g. another port for fluid infusion, and/or one or more ports for cable connections to other types of monitoring equipment, e.g. for measurement of cardiac output, oximetry, or insertion of a cardiac pacing wire.

By way of example only, the following references provide further background information and details of insertion techniques, characteristic pressure waveforms, and indications for RHC and PA catheterization:
1) Jeremy Fernando, "Pulmonary Artery Catheters", updated 22 Dec. 2014 (http://lifeinthefastlane.com/ccc/pulmOnry-artery-catheters/);
2) "Swan-Ganz—right heart catheterization", NIH National Library of Medicine, online Medical Encyclopedia, Update Date Aug. 12, 2014 (https://www.nlm.nih.gov/medlineplus/ency/article/003870.htm);
3) "Pulmonary artery catheter", Wikipedia, version last modified 8 May 2016 (https://en.wikipedia.org/wiki/Pulmonary_artery_catheter);
4) "Invasive Hemodynamic Monitoring: Physiological Principles and Clinical Applications" pp. 12-15; Jan M. Headley, RN, BS, CCRN, Edwards Life Sciences; Irvine, Calif., © 2002 (http://ht.edwards.com/resourcegallery/prodcts/swanganz/pdfs/invasivehdmphysprincbook.pdf);
5) B. Paunovic et al., "Pulmonary Artery Catheterization", (c) 2011, updated 3 Jan. 2016 (http://emedicine.medscape.com/article/1824547 (c) 2011);
6) "Right Heart Catheterization", Johns Hopkins Medicine Health Library, version downloaded August 2016 (http://www.hopkinsmedicine.org/healthlibrary/test_procedures/cardiovascular/right_heart catheterization 135.40/);
7) "Comparing FFR Tools New wires Pressure Microcatheter", M. Kern, Cath Lab Digest, Volume 24, Issue 5, May 2016 (http://www.cathlabdigest.com/article/Comparing-FFR-Tools-New-Wires-Pressure-Microcatheter);

Conventional balloon tipped PA catheters that use a fluid filled catheter, which is coupled to an externally placed pressure transducer, are relatively inexpensive and durable. However, they measure pressure only at a single point, i.e. at the tip of the catheter. Thus, the cardiologist must reposition the catheter, i.e. by pushing and pulling the catheter tip back and forth to position tip to make pressure measurements at different locations within the heart. During this procedure, there is some risk that repeatedly advancing and pulling-back the catheter for repositioning tip of the catheter for pressure sensing will interfere with, or disrupt, normal operation of the heart, e.g. cause cardiac arrhythmias (such as atrial or ventricular fibrillation), interfere with opening and closing of the heart valves, or risk damage to the heart tissues.

Also, pressure sensing catheters have limited accuracy. Measurements may be affected by technical limitations such as reflection of the pressure wave at the tip and distortion if the catheter is kinked or sharply bent. Inertial artefacts and slow dynamic response (time lag, damping, hysteresis, resonances, frequency filtering) can distort the waveform, in time and amplitude, as it travels through the fluid filled lumen (de Vecchi et al., "Catheter induced Errors in Pressure Measurements in Vessels: An in-vitro and numerical study" IEEE Transaction on Biomedical Engineering, Vol. 61, No. 6, June 2014). Measurement errors as much as 20 mmHg have been reported (see ref. 2 in Robert G. Grey et al., "Feasibility of In Vivo Pressure Measurement using a pressure tip catheter via transventricular puncture", ASAIO J. 2010 56(3) 194-199. This reference also compares limitations of a Pressure Tipped Catheter (PTC) using a piezo-electric pressure sensor and a conventional fluid filled pressure sensing catheter.

Limitations of pressure sensing catheters with externally placed transducers are also discussed in United States patent application publication no. US2011/004198, to Hoch, which discloses a central venous catheter (CVC) using a piezo-electric pressure sensor. However, electrical pressure sensors of this type have some drawbacks for in vivo applications, where long thin electrical wires are carrying small electrical signals in humid environment, e.g. requirement for electrical isolation of electrical components, significant electrical drift and temperature sensitivity and electrical interference, such as, cross-talk between wires from multiple electrical sensors and from external electromagnetic sources within the operating room.

Thus, there is a need for improved or alternative PA catheters for direct measurements of cardiovascular parameters, including blood pressure measurements, during RHC and PA catheterization procedures.

An object of the present invention is to provide for improvements or alternatives to known systems and apparatus comprising multi-sensor catheters or multi-sensor guidewires.

SUMMARY OF INVENTION

The present invention seeks to mitigate one or more disadvantages of known systems and apparatus comprising multi-sensor catheters or multi-sensor guidewires for measuring cardiovascular parameters, and in particular to provide systems and apparatus with particular applicability for measurements of hemodynamic parameters during right heart catheterization (RHC) and PA catheterization.

In one aspect, the present invention seeks to provide a multi-sensor catheter with particular applicability for measurements of hemodynamic parameters during right heart and pulmonary artery catheterization.

A first aspect of the invention provides a multi-sensor catheter for right heart and pulmonary artery catheterization, comprising:
a length of multi-lumen catheter tubing extending between a proximal end and a distal end, having an outside diameter of ≤8 French, and the distal end comprising an atraumatic tip;

a plurality of optical sensors and a plurality of optical fibers; a sensor end of each optical fiber being attached and optically coupled to an individual one of the plurality of optical sensors;

each optical sensor and its optical fiber being inserted into a respective lumen of the multi-lumen catheter tubing, the sensors being spaced apart lengthwise to provide a sensor arrangement with said plurality of optical sensors positioned at respective sensor locations spaced apart lengthwise within a distal end portion of the catheter tubing;

a proximal end of each of the plurality of optical fibers being coupled to an optical input/output connector at the proximal end of the catheter for connection to an optical control system; and the plurality of optical sensors of the sensor arrangement comprising at least three optical pressure sensors at respective sensor locations spaced apart lengthwise along said length of said distal end portion, with an aperture in the catheter tubing adjacent each optical pressure sensor for fluid contact; and wherein the pressure sensor locations and spacings are configured to place at least one pressure sensor in each of the right atrium, the right ventricle and the pulmonary artery during right heart catheterization, for concurrent blood pressure measurements at each pressure sensor location.

The multi-sensor catheter may further comprise another lumen having a proximal port and an opening at the distal tip of the catheter tubing, said lumen having a diameter which accepts a guidewire, e.g. a standard 0.025 inch (0.625 mm) guidewire, to enable the catheter to be inserted over the guidewire. For example, to facilitate insertion into the PA, the guidewire is first steered into the RV and PA, and then the catheter is introduced over the guidewire. The latter facilitates introduction of the PA catheter by a more tortuous route, for example when it is introduced from the inferior vena cava.

The multi-sensor catheter may further comprise an inflatable balloon near the distal tip, the catheter tubing further comprising a balloon inflation lumen, the inflatable balloon being coupled by the balloon inflation lumen to a balloon inflation port at the proximal end of the catheter tubing. An inflatable balloon tip allows for introduction of the tip of the catheter to be flow directed, i.e. the balloon is floated and guided by blood flow into the PA, and for measurement of the PA pressure waveform and PCWP waveform, similar to a conventional PA catheter.

When the multi-sensor catheter comprises a balloon tip and a guidewire lumen, a guidewire may be used to facilitate insertion and/or the balloon may be inflated for flow directed insertion. The guidewire lumen is preferably a central lumen. This lumen may also be used for blood sampling at the tip of the catheter, e.g. for measurement of $SvO_2$ or measurement of cardiac output by the Fick method.

In some embodiments, for direct measurement of blood flow within the PA, the plurality of optical sensors further comprises an optical flow sensor. For example, the flow sensor comprises an optical thermo-dilution or an optical thermo-convection sensor positioned proximal to the distal tip for placement in the PA and the catheter tubing further comprises a fluid injection lumen having an aperture positioned for fluid injection into the right atrium and the fluid injection lumen being coupled at the proximal end of the multi-lumen catheter to a fluid injection port.

The multi-lumen catheter tubing may, for example, have an outside diameter of between 4 and 7 French and more preferably has an outside diameter of 6 French (2.000 mm) or less. The optical pressure sensors are preferably Fabry-Perot (FP) Micro-Opto-Mechanical System (MOMS) sensors. These optical pressure sensors comprise, for example, standard optical fibers of 0.155 mm diameter and FP MOMS pressure sensors of 0.260 mm diameter at the sensor end of the fiber for sensing pressure. When the catheter has a guidewire lumen which accepts a guidewire, e.g. a standard guidewire of up to 0.025 inch (0.625 mm) diameter, and the sensor arrangement comprises three optical pressure sensors and an optical flow sensor, and a fluid injection lumen, this four optical sensor arrangement can be accommodated within a multi-lumen catheter having an outside diameter of the multi-lumen tubing of approximately 6 French. The guidewire lumen is preferably a central lumen of the multi-lumen catheter, and the other lumens are arranged symmetrically around the central lumen. With smaller diameter optical sensors and fibers, and/or for use with a smaller diameter guidewire, smaller diameter multi-lumen catheter tubing may be used. PA catheters for insertion through one of the larger veins in the neck or groin are typically in the range from 4 to 8 French, with 6 or 7 French being commonly used. Smaller gauge catheters may be preferred for convenience or patient comfort, e.g. to allow for insertion through one of the veins in the upper or lower arm, such as the median cubital vein. Smaller diameter catheters may be required for pediatric use or neonatal use.

In an embodiment, the proximal end of the multi-lumen catheter comprises a connection hub, through which each lumen of the multi-lumen catheter is connected to a "tail" comprising an individual length of flexible tubing and respective individual proximal ports. The proximal ports for each optical sensor comprising said optical input/output connector, and the optical fibers for each optical sensor extending through from the optical sensor through its respective individual lumen of the multi-lumen catheter tubing, through the hub and flexible tubing to the respective optical input/output connector for connection to the optical control system.

Optionally, the catheter comprises radiopaque markers at intervals along the length of the catheter to facilitate location of each sensor in use, e.g. by conventional radio-imaging techniques. For example, markers may be placed at regular intervals along the length, or markers are placed near each sensor. A radiopaque marker may also be placed at the tip or near the balloon.

The catheter may comprise one or more additional lumens with proximal ports, which are provided for fluid injection or fluid infusion, with respective distal apertures located for injection or infusion of fluid the right atrium during use. One or more additional lumens and respective proximal ports may optionally be provided for other purposes, if required.

Embodiments of the present invention provide improved or alternative guidewire directed catheters and flow directed balloon catheters that enable direct measurements of cardiovascular parameters, including measurement of pressure concurrently within the RA, RV, and PA, during RHC and PA catheterization procedures.

Another aspect of the invention provides a multi-sensor catheter for right heart and pulmonary artery catheterization in pediatric or neonatal patients, comprising:

a length of multi-lumen catheter tubing extending between a proximal end and a distal end, having an outside diameter of ≤3 French, and the distal end comprising an atraumatic tip;

a plurality of optical sensors and a plurality of optical fibers; a sensor end of each optical fiber being attached and optically coupled to an individual one of the plurality of optical sensors;

each optical sensor and its optical fiber being inserted into a respective lumen of the multi-lumen catheter tubing, the sensors being spaced apart lengthwise to provide a sensor arrangement with said plurality of optical sensors positioned at respective sensor locations spaced apart lengthwise within a distal end portion of the catheter tubing;

a proximal end of each of the plurality of optical fibers being coupled to an optical input/output connector at the proximal end of the catheter for connection to an optical control system; and the plurality of optical sensors of the sensor arrangement comprising at least two optical pressure sensors at respective sensor locations spaced apart lengthwise along said length of said distal end portion, with an aperture in the catheter tubing adjacent each optical pressure sensor for fluid contact; and wherein the pressure sensor locations and spacings are configured to measure concurrent pressure waveforms for at least two locations within the heart and pulmonary artery comprising a right atrial pressure waveform, a right ventricular waveform, and a pulmonary artery waveform, a pulmonary capillary wedge position waveform, to provide concurrent blood pressure measurements at each optical pressure sensor location.

A further aspect of the invention comprises a control system for multi-sensor catheters and multi-sensor guidewires, such as, the multi-sensor PA catheters disclosed herein.

The control system comprises a light source and detector, and an optical interface for coupling, via respective input/output ports, to each of the optical fibers and optical sensors of a multi-sensor catheter or multi-sensor guidewire; data storage and processing means configured for processing optical data indicative of pressure values and optionally, optical or electrical data indicative of flow velocity values; and wherein, for right heart catheterization and pulmonary artery catheterization, the processing means is further configured for graphically displaying pressure data comprising a plurality of concurrent blood pressure waveforms. Thus, when the multi-sensor catheter comprises at least three optical pressure sensors, the system can process optical data from each sensor and display concurrent blood pressure waveforms from the right atrium, right ventricle and pulmonary artery.

The concurrent blood pressure waveforms for each optical sensor may be displayed together for comparison, or displayed individually, for one or more time intervals, and during one or more cardiac cycles. Optionally, graphical flow velocity data may also be displayed concurrently. Advantageously, the processing means is further configured to derive and display hemodynamic parameters from the blood pressure data and flow velocity data. For example, during right heart and pulmonary artery catheterization with a multi-sensor catheter as disclosed herein comprising at least three optical pressure sensors, in addition to displaying blood pressure waveforms from the right atrium, right ventricle and pulmonary artery, a plurality of numeric values such as peak pressures, mean pressures, peak-to-peak pressure differentials for each curve, and pressure differentials or gradients between the right atrium and right ventricle, and between the right ventricle and pulmonary artery can be displayed in real time.

Correspondingly, in another exemplary embodiment, in use of a multi-sensor guidewire during TAVR, e.g. to assess functioning of the aortic valve, before and after a TAVR procedure, the system may display numeric values based on pressure waveforms from the aorta and the left ventricle. For example, in addition to displaying pressure waveforms from the aorta and the left ventricle, the system may display a plurality of numeric values such as peak pressures, mean pressures, peak-to-peak pressure differentials for each curve, and pressure differentials or gradients between the aorta and the left ventricle. The system may also compute a parameter such as an aortic regurgitation index (ARi), and display the ARi value in real time.

Accordingly, another aspect of the invention provides a computer program product embodied as a non-transitory computer readable medium storing instructions, for execution in a processor of a control system for a multi-sensor catheter or a multi-sensor guidewire, for processing optical data received concurrently from a plurality of optical sensors of the multi-sensor catheter or a multi-sensor guidewire, said optical data being indicative of blood pressure, and displaying a corresponding plurality of blood pressure waveforms, and optionally flow velocity data, and displaying numeric data relating to selected hemodynamic parameters and indexes.

Thus, apparatus and systems comprising a multi-sensor PA catheter are provided that mitigate one or more problems with known systems and apparatus for RHC and PA catheterization, which allow for diagnostic measurements and monitoring of hemodynamic parameters, including measurement of blood pressure concurrently at multiple locations within the right heart and PA.

The foregoing and other objects, features, aspects and advantages of the present invention will become more apparent from the following detailed description, taken in conjunction with the accompanying drawings, of embodiments of the invention, which description is by way of example only.

BRIEF DESCRIPTION OF THE DRAWINGS

In the drawings, identical or corresponding elements in the different Figures have the same reference numeral.

DETAILED DESCRIPTION OF EMBODIMENTS

Figure 1:
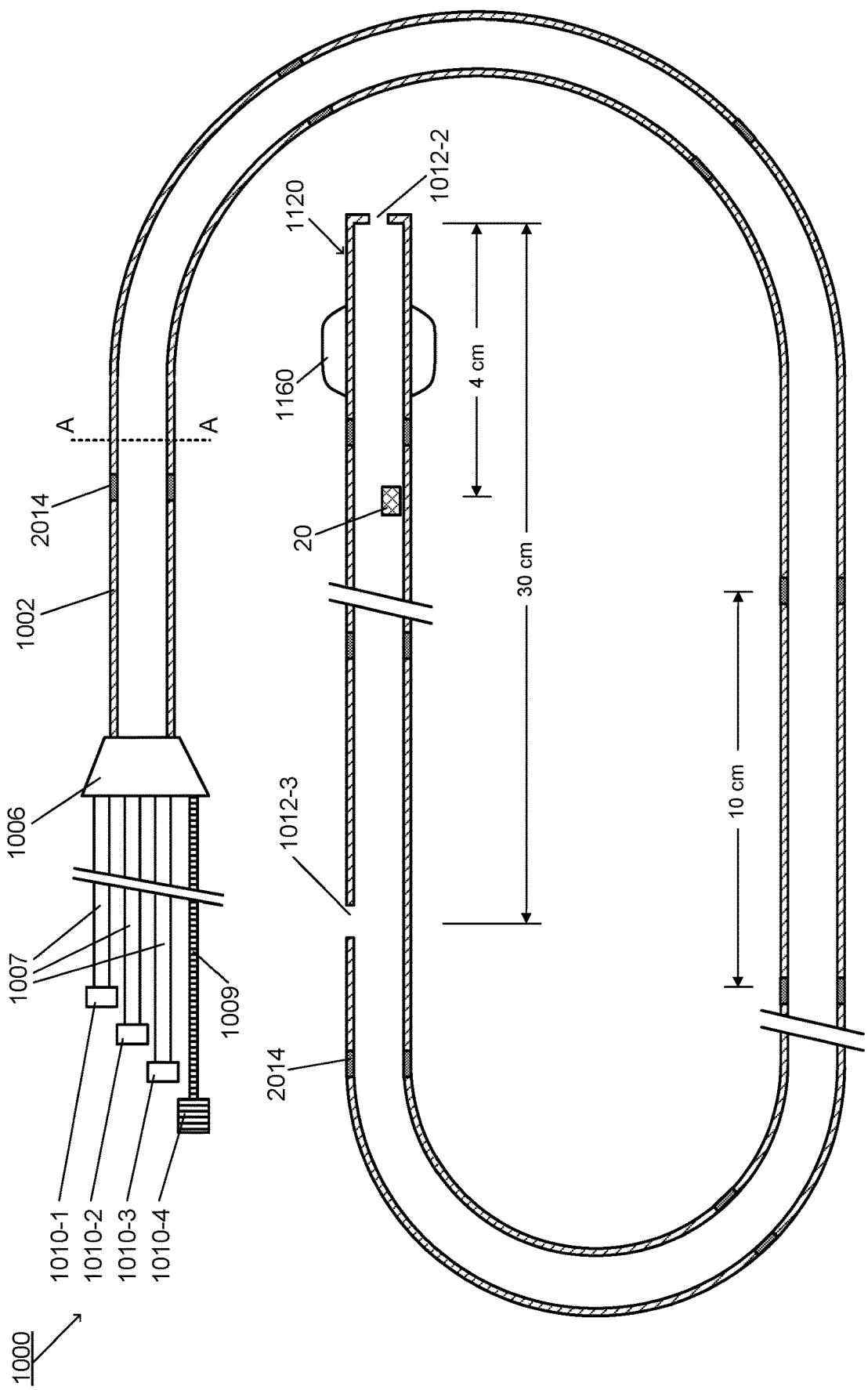
FIG. 1 (Prior Art) shows a schematic longitudinal cross-sectional view of a known type of conventional PA catheter, which may be referred to as a Swan Ganz catheter.
Figure 2:
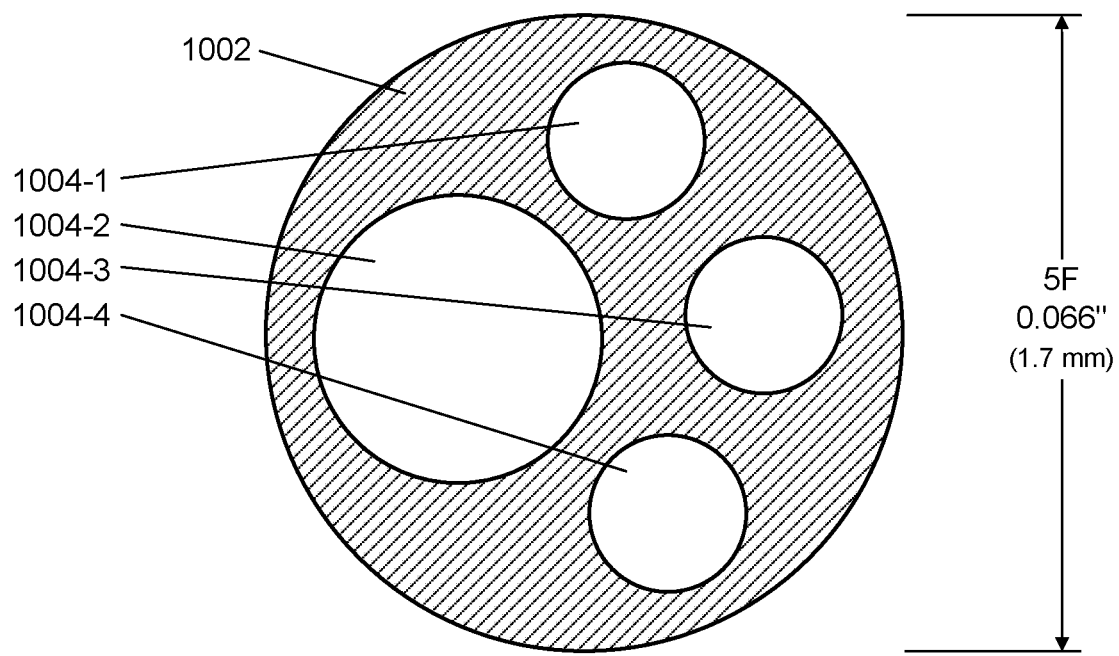
FIG. 2 (Prior Art) shows an enlarged transverse cross-sectional view of the PA catheter illustrated in FIG. 1 taken through plane A-A of FIG. 1 to show the lumens of the multi-lumen catheter tubing.

As illustrated schematically in the longitudinal cross-sectional view shown in FIG. 1, a conventional PA catheter 1000, which may be referred to as a Swan Ganz catheter, comprises a length of multi-lumen catheter tubing 1002 having at its distal end 1120 an inflatable balloon 1160. The catheter typically comprises a multi-lumen catheter tubing 1002, such as illustrated in FIG. 2, which is a cross-sectional view through plane A-A of FIG. 1. By way of example, the catheter tubing shown in FIG. 2 has four lumens 1004-1, 1004-2, 1004-3 and 1004-4, and an outside diameter of 5 French. Referring back to FIG. 1, there is a hub 1006 at the proximal end of the catheter with individual proximal ports 1010-1, 1010-2, 1010-3, and 1010-4. Ports 1010-1, 1010-2, 1010-3 are coupled by individual lengths of flexible tubing 1007 through the hub 1006 to respective lumens 1004-1, 1004-2 and 1004-3 of the catheter tubing 1002. Port 1010-4 is an electrical connector for a thermistor 20 which is located within the fourth lumen 1004-4 proximal to the balloon tip 1160, towards the distal end. Electrical connections for the thermistor 20 extend through lumen 1004-4 from the thermistor 20 to an electrical cable 1009 extending from the hub 1006. For simplicity of illustration of the longitudinal cross-sectional view shown in FIG. 1, the inner walls of the lumens are not shown.

Traditionally, the multi-lumen catheter tubing 1002 of a Swan Ganz catheter is colored yellow and each of the ports 1010-1 to 1010-4 is color coded. A first lumen 1004-1 provides for inflating the balloon and has a corresponding proximal port 1010-1 for coupling to an air filled syringe for inflating and deflating the balloon. The balloon inflation port is conventionally colored red. The balloon 1160 typically has a volume of 0.5 ml to 1.5 ml and is connected to the balloon inflation lumen 1004-1. A second lumen 1004-2 is has an aperture 1012-2 opening at the distal tip 1120 and is connected at the proximal end to a proximal port 1010-2 (conventionally colored yellow) for connection to an externally placed pressure transducer, so that, when this lumen is filled with fluid, the blood pressure at the tip 1120 can be sensed. This port and lumen may also be used for sampling of blood at the tip of the catheter. For measurement of flow by thermo-dilution using the thermistor 20, there is third lumen 1004-3, which has a proximal injectate port (conventionally coloured blue) to allow for injection of a bolus of cold thermo-dilution fluid; this lumen has an injectate opening 1012-3 a distance of approximately 30 cm from the distal tip 1120. The fourth lumen 1004-4 accommodates the thermistor 20, i.e. an electrical temperature sensor, which is typically located at a distance of about 4 cm from the distal tip 1120; the electrical wires (not shown in FIG. 1) for the thermistor 20 extend through lumen 1004-4 to a proximal port 1010-4 (conventionally colored yellow) which comprises an electrical connector for the thermistor T. In this example, the second lumen 1004-2, which has an opening 1012-2 at the distal tip 1120 and respective proximal port 1010-2 has a larger diameter to allow for insertion of a guidewire, e.g. a standard 0.025 inch or 0.018 inch guidewire, to assist with introduction of the PA catheter into the right heart.

Figure 3:
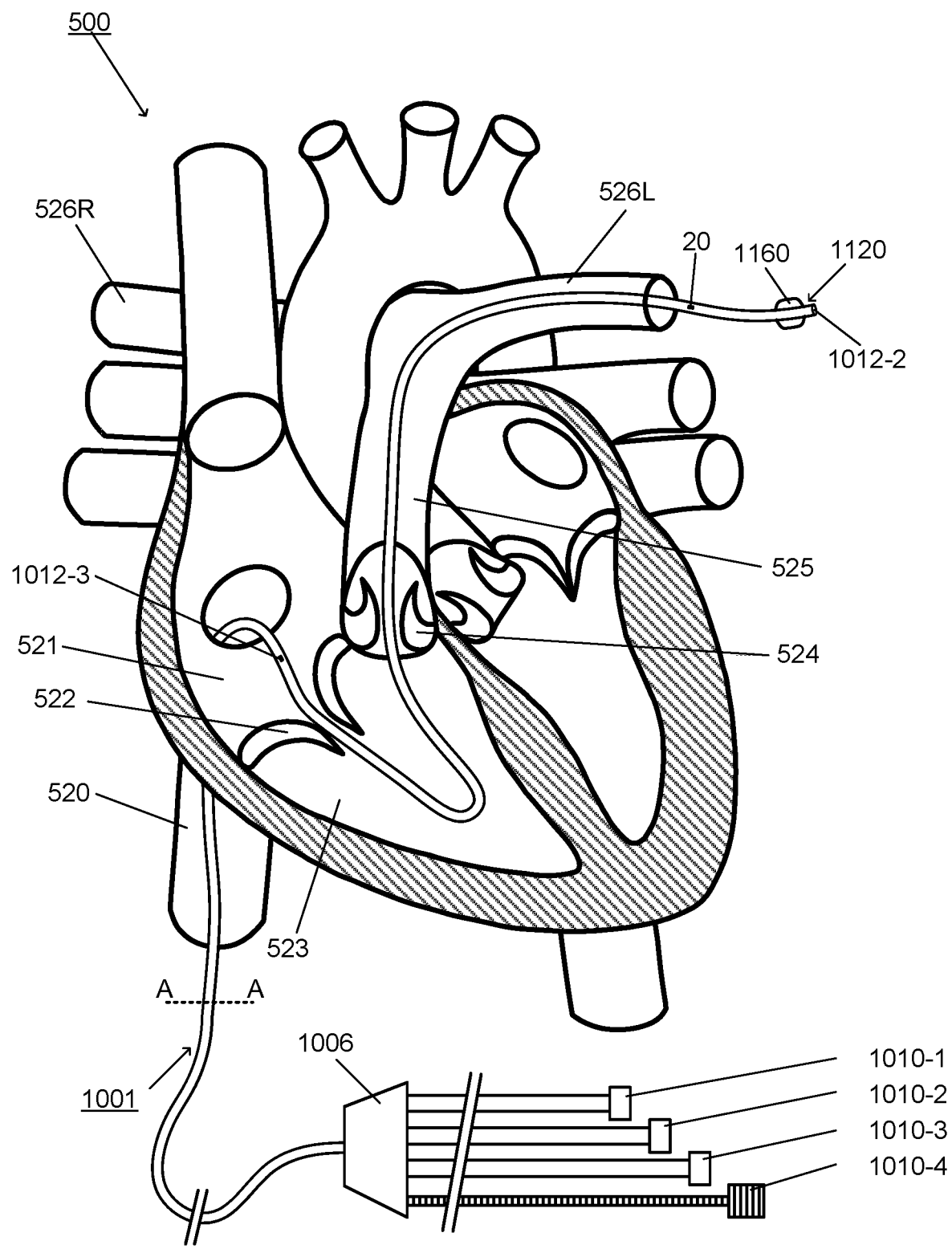
FIG. 3 (Prior Art) shows schematic partial cross-sectional view of a human heart to illustrate placement of a conventional PA catheter within the right heart and the PA for measurement of pressure in the PA and for measurement of blood flow by thermo-dilution.

FIG. 3 illustrates schematically a partial cross-sectional view of a human heart 500 with a PA catheter 1001 positioned within the right heart and left branch of the PA. The PA catheter 1001 is similar to that shown in FIGS. 1 and 2 comprising four lumens, i.e. one for balloon inflation, one for pressure sensing, one for the thermistor and one for fluid injection for measurement of flow by thermo-dilution. Similar to the catheter shown in FIG. 1, the four lumens are connected through a hub 1006 to proximal ports 1010-1, 1010-2, 1010-3 and 1010-4. The first lumen 1004-1 opens to the inflatable balloon 1160 and the first lumen is connected to the balloon inflation/deflation port 1010-1 for connection to an air filled syringe; the second lumen has an opening 1012-2 at the distal tip 1120 and a distal port 1010-2. The distal port 1010-2 that is used for the guidewire insertion can also be used either for connection to an external pressure transducer for measurement of blood pressure at the distal tip 1120, or, for blood sampling, such as for measuring mixed venous oxygen saturation ($SvO_2$). The third port 1010-3 is the proximal injection port which is connected to the third lumen 1004-3 (FIG. 2) for fluid injection into the right atrium 521 through opening 1012-3. The fourth port 1010-4 comprises an electrical connector for the thermistor 20 which is located in the fourth lumen 1004-4 near the distal tip 1120.

To position the PA catheter 1001 as illustrated schematically in FIG. 3, the catheter tip 1120 is introduced into the right atrium (RA) 521, e.g. in this example upwards through the inferior vena cava 520, and through the atrioventricular (tricuspid) valve 522 and into the right ventricle (RV) 523. During introduction, partial inflation of the balloon 1160 allows for blood flow directed insertion. That is, with partial inflation of the balloon 1160 in the right ventricle 523, the tip 1120 of the catheter tends to be drawn by the blood flow through the pulmonic valve 524 into the PA 525 and then from the PA towards the right or left branches 526L and 526R of the PA, and towards smaller pulmonary vessels which lead to the lungs. Pressure sensing at the tip is achieved by the fluid filled lumen 1004-2 which has opening 1012-2 at the distal tip 1120, and a proximal port 1010-2 which is connected to the externally placed pressure transducer for monitoring pressure at the catheter tip 1120. The port 1010-4 provides for electrical connections for the thermistor 20 (T), which located about 4 cm proximally from the balloon tip 1160, for measurement of blood flow by thermo-dilution. As illustrated schematically in FIG. 3, the opening 1012-3 of the fluid injection lumen is positioned to allow for injection of a bolus of cold fluid into the right atrium of the heart, for detection of a temperature change by the thermistor 20 (T) when the cold fluid reaches the PA 525 and its left and right branches 526L and 526R, to measure blood flow by a conventional thermo-dilution technique.

Figure 4:
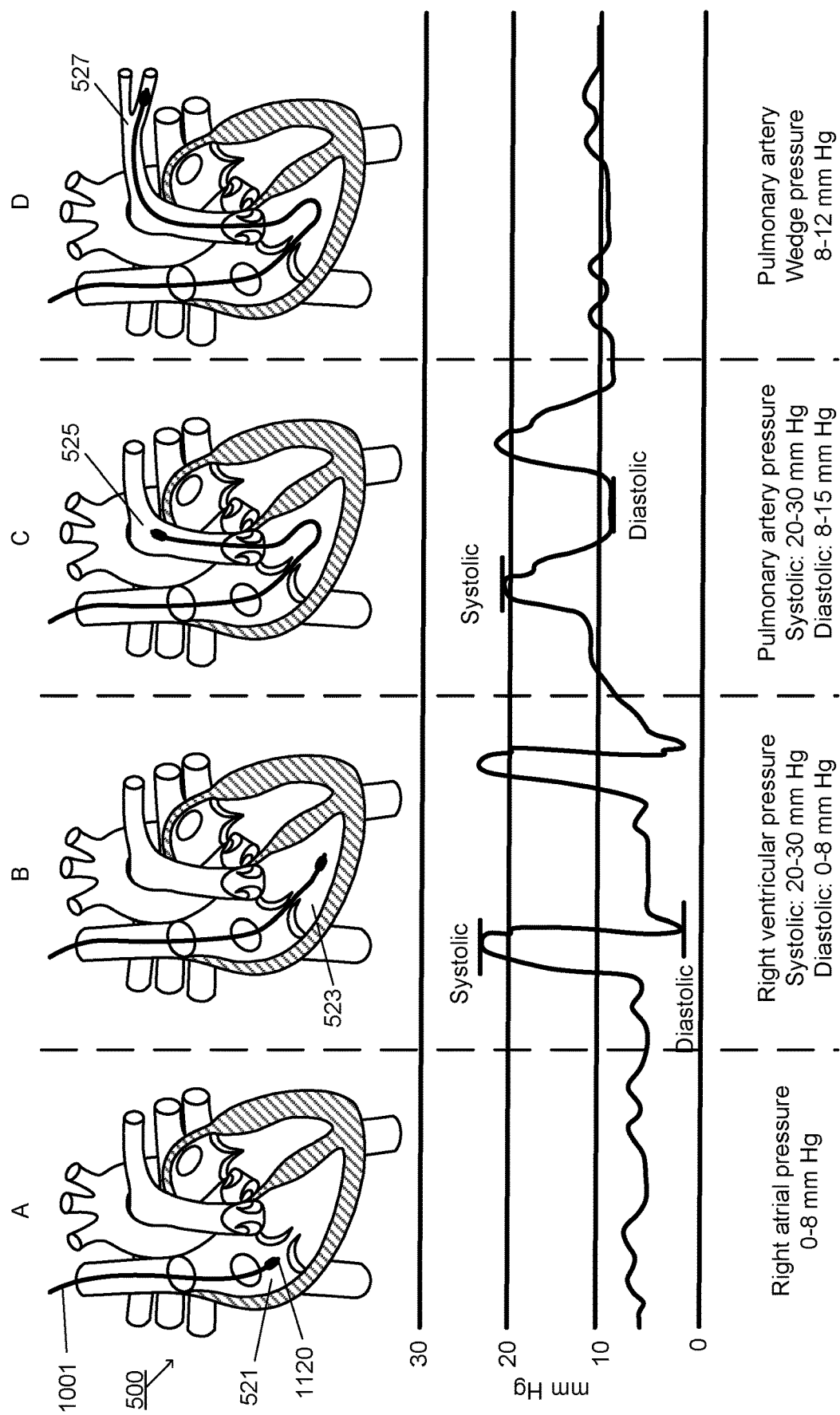
FIG. 4 (Prior Art) shows schematic diagrams of a human heart to illustrate schematically placement of the conventional PA catheter within the right heart and PA for pressure measurements, at each the following positions: A. in the right atrium (RA); B. in the right ventricle (RV); C. in the pulmonary artery (PA); and D. in a pulmonary capillary wedge position (PCWP); the underlying plots show examples of a sequence of typical blood pressure waveform for each of positions A, B, C and D.

In use of the PA catheter 1001, as illustrated in FIG. 4 (Prior Art), when the tip 1120 of the catheter 1001 is first introduced into the heart 500, e.g., through the superior vena cava as illustrated, and into the RA 521 (position A), a pressure measurement is made in the RA to assess the RA waveform. Then the tip of the catheter is advanced through the tricuspid valve 522 into the RV 523 (position B), and a pressure measurement is made within the RV to assess the RV waveform. The balloon is partially inflated so that the blood flow draws the balloon from the right ventricle 523, through the pulmonic valve 524 into the PA 525. When the tip of the catheter is in the PA (position C), the balloon is deflated, and another pressure measurement is made to assess the PA waveform. The tip of the catheter is then allowed to be drawn further into the PA and the balloon at the tip of the catheter is further inflated. When the inflated balloon wedges in a smaller branch 527 of the pulmonary vessels (position D) another pressure measurement is made, called the PA occlusion pressure, or pulmonary capillary "wedge" pressure (PCWP) waveform. PCWP provides an indirect measure of the left atrial pressure (LAP) and left ventricular end-diastolic pressure (LVEDP). As illustrated by the blood pressure waveform in the low part of FIG. 4, as the catheter tip is advanced, the observed waveform changes sequentially and show the transition from a RA pressure waveform, a RV pressure waveform, a PA pressure waveform and then a PCWP waveform. The cardiac output (CO), which is the amount of blood that the heart pumps per minute, may also be determined during a right-heart and PA catheterization. Pressure measurements may be made before and after administration of intravenous (IV) heart medications. The catheter may need to be repositioned several times to allow for several pressure measurements to be made at each of the different locations A, B, C and D within the heart and PA.

Limitations of conventional PA catheters of this type include:
Pressure measurements are made by a fluid filled pressure sensing catheter
Pressure is transmitted through fluid filled lumen to a remote pressure transducer; pressure measurements are not always accurate.
Pressure is measured at the distal tip only, so pressure can be measured only at one point or location at a time.
Pressure measurements are sensitive to relative positioning and re-positioning of the catheter and pressure transducer, e.g. raising or lowering it relative to the heart in order to set the zero pressure (0 cm $H_2O$) on the transducer.
Kinking or bending of the catheter may dampen the characteristic waveforms seen at each position;
There is time lag (and hysteresis) between pressure being applied to the opening at the tip of the pressure sensing lumen and transmission of pressure through the fluid filled lumen to the remote transducer.
Pullback and repositioning of the catheter for multiple measurements may cause cardiac arrhythmias.

A system and apparatus comprising a multi-sensor catheter for use in cardiology, which may include diagnostic measurements of cardiovascular parameters during right heart and PA catheterization, according to an embodiment of the present invention will be illustrated and described, by way of example, with reference to a system 2000 comprising a multi-sensor PA catheter 2001, illustrated schematically in FIGS. 5 to 9.

Figure 5:
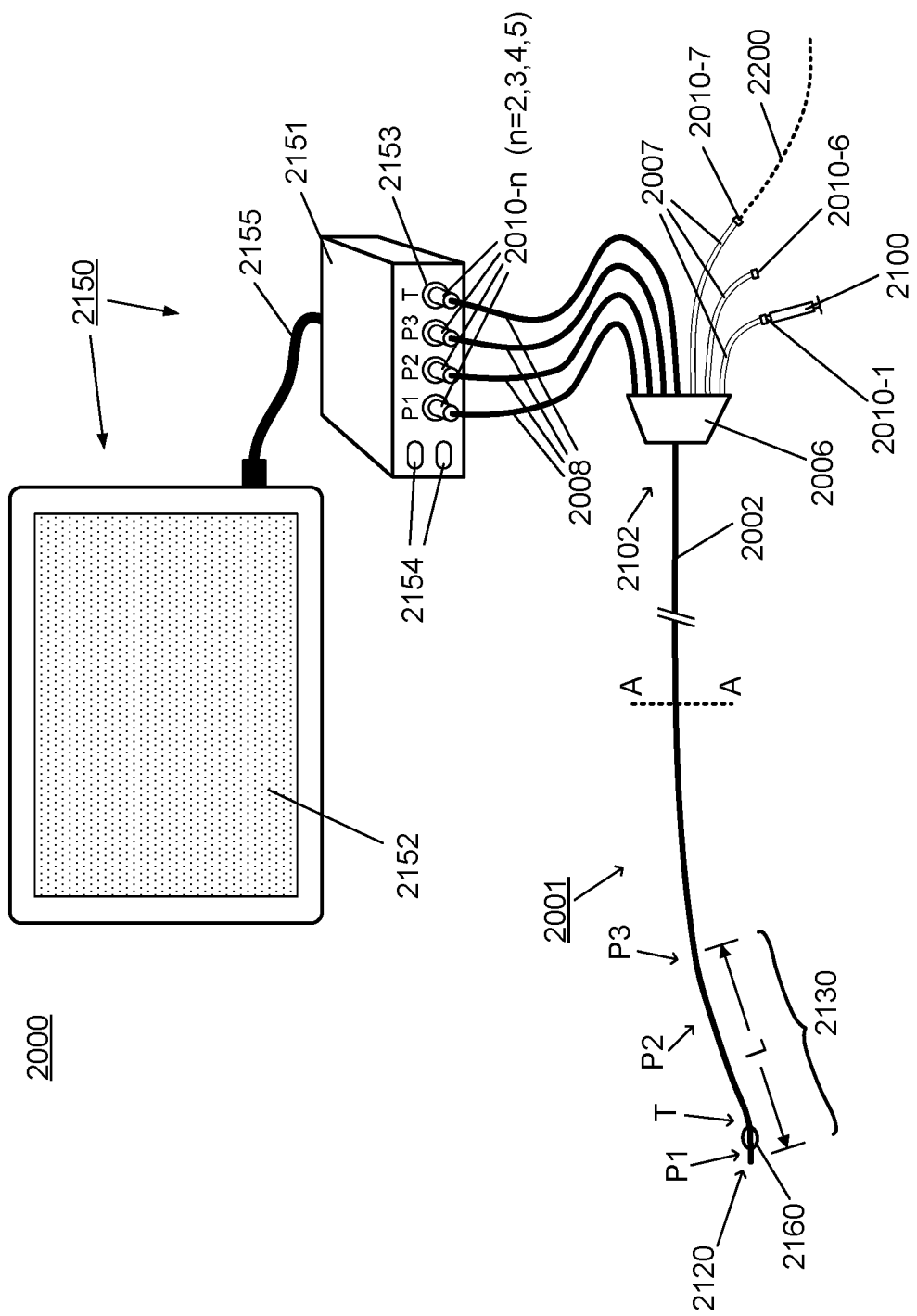
FIG. 5 illustrates schematically a system according to a first embodiment, comprising an apparatus for right heart and PA catheterization comprising a multi-sensor PA catheter, which is optically coupled to a control unit.

Firstly, referring to FIG. 5, this schematic diagram represents the system 2000 comprising an apparatus 2001 comprising a multi-sensor catheter for right heart and PA catheterization procedures, coupled to a control system 2150, which comprises a control unit 2151 and user interface, such as the illustrated touch screen display 2152. The multi-sensor catheter 2001 comprises some components of a conventional PA catheter, including multi-lumen catheter tubing 2002. In the multi-sensor catheter of this embodiment, the catheter tubing comprises seven lumens 2004-1 to 2004-7, as illustrated in the transverse cross-sectional view in FIG. 7, which is a cross-section through A-A of FIGS. 5, 6 and 9. Typically, the catheter tubing 2002 has an outside diameter in the range of about 3-8 French (see Table 1 below for equivalent dimensions in mm and inches), and extends to an atraumatic flexible tip 2120 comprising an inflatable balloon 2160, as shown schematically in FIGS. 5 and 6.

TABLE 1

| French (Gauge) | Diameter (mm) | Diameter (inches) |
| --- | --- | --- |
| 2 | 0.667 | 0.027 |
| 3 | 1.000 | 0.039 |
| 4 | 1.333 | 0.053 |
| 5 | 1.667 | 0.066 |
| 6 | 2.000 | 0.079 |
| 7 | 2.333 | 0.092 |
| 8 | 2.667 | 0.105 |

By way of example, the catheter tubing may typically be about 110 cm in length from the distal tip 2120 to the proximal end, which comprises a connection hub 2006. This length is suitable for introduction of the catheter into the right heart and PA through the superior vena cava (e.g. reached through the subclavian vein or interior jugular vein in the neck, or through the median cubital vein in the arm) or the inferior vena cava (e.g. reached through a femoral vein). For some applications, the catheter length may be shorter, e.g. 60 cm, or longer than 110 cm.

Figure 6:
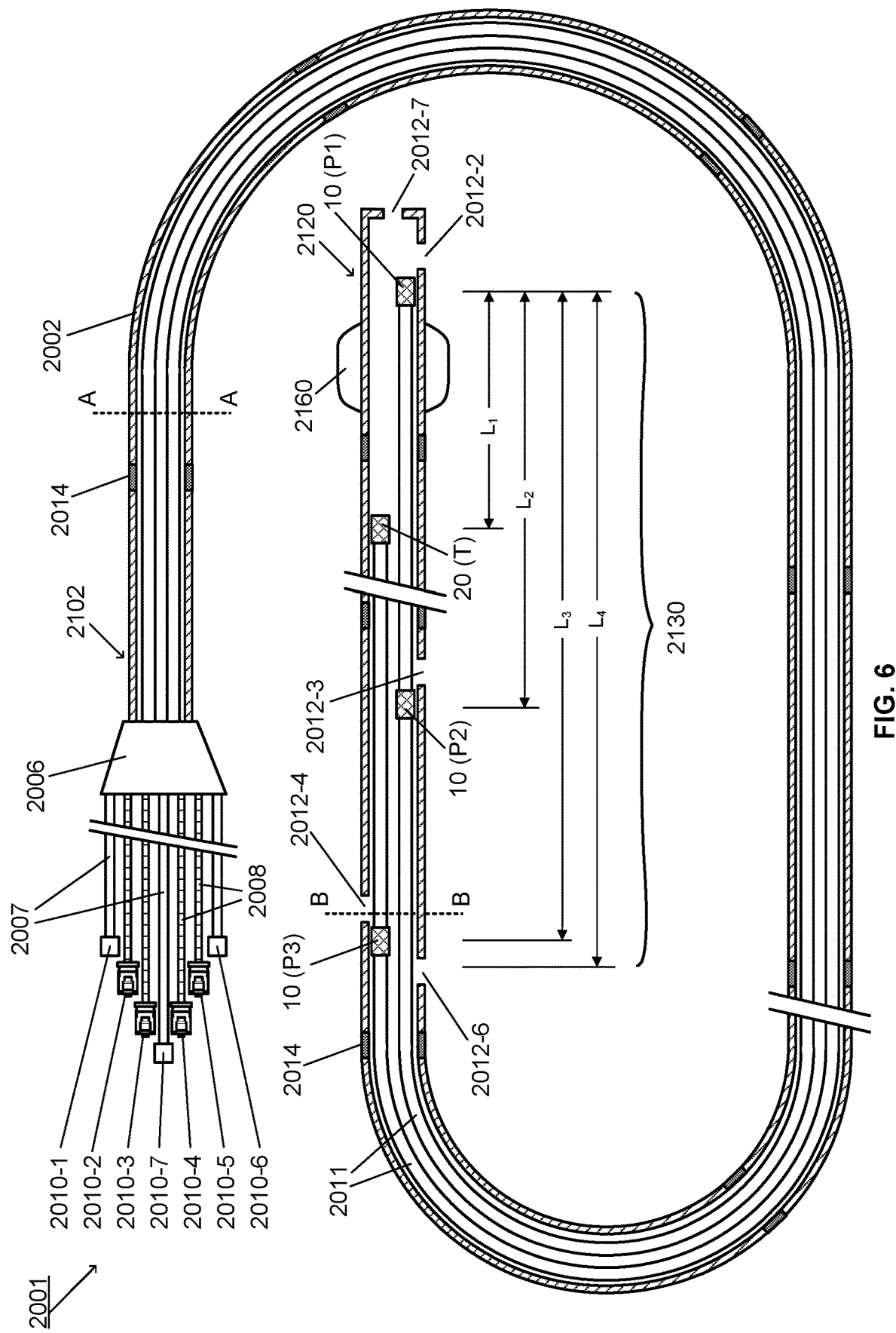
FIG. 6 shows a schematic longitudinal cross-sectional view of an apparatus for right heart and PA catheterization comprising a multi-sensor PA catheter according to the first embodiment of the present invention.

The PA catheter 2001 differs from a conventional PA catheter, in that, internally, as illustrated schematically in the longitudinal cross-sectional view in FIG. 6, it also contains a multi-sensor arrangement comprising a plurality of optical pressure sensors 10 and an optical temperature sensor 20, and respective optical fibers 2011. The optical sensors 10 and 20 are not externally visible in FIG. 5, so the sensor positions are indicated schematically by P1, P2, P3 for the optical pressure sensors and T for the optical temperature sensor. The sensor positions P1, P2, P3 and T are located along a length L distal end portion 2130, near the distal tip 2120. As illustrated schematically in FIG. 5, the connection hub 2006 provides connection ports 2010-n, where n=1 . . . 7, for each of the seven lumens. Four of the connection ports, 2010-2, 2010-3, 2010-4, 2010-5 are optical connectors which are coupled via flexible optical connections 2008 through the hub 2006 to the optical fibers and sensors within their respective lumens, i.e. lumens 2004-2, 2004-3, 2004-4, 2004-5 shown in the transverse cross section in FIG. 7. The optical connectors each for the four optical sensors (P1, P2, P3 and T) plug into corresponding optical ports 2153 of the optical controller 2151 shown in FIG. 5.

Figure 7:
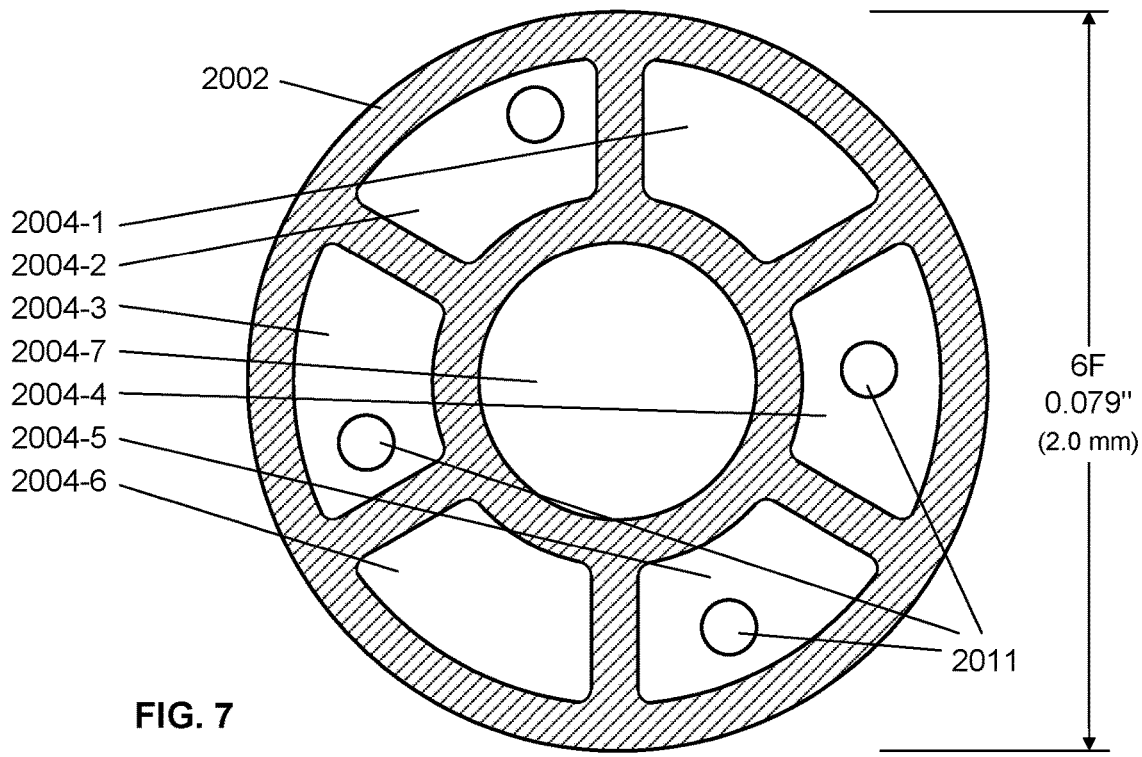
FIG. 7 shows an enlarged axial cross-sectional view of the multi-lumen catheter illustrated in FIG. 6 taken through plane A-A of FIG. 6.
Figure 8:
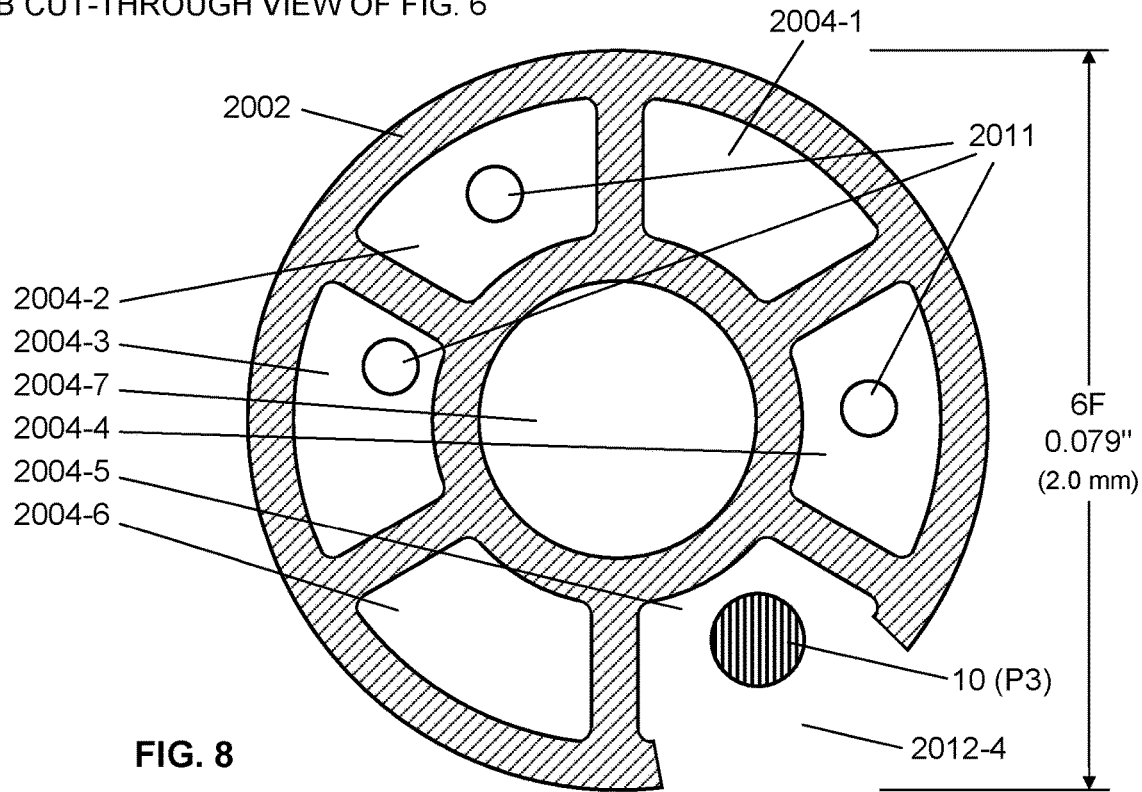
FIG. 8 shows an enlarged axial cross-sectional view of the multi-lumen catheter illustrated in FIG. 6 taken through plane B-B of FIG. 6.

Referring to the schematic longitudinal cross-sectional view shown in FIG. 6, and the transverse cross-sectional view shown in FIG. 7, for simplification of illustration, the internal walls of the lumens 2004-1 to 2004-7 are omitted from FIG. 6 and only the optical fibers 2011 and sensors 10 and 20 are shown within the catheter tubing; elements shown in FIG. 6 are not drawn to scale. Thus, in description of FIG. 6, references to the lumens 2004-1 to 2004-7 are made based on FIG. 7. Also, by way of example, FIG. 7 shows typical dimensions for catheter tubing comprising seven lumens and having an outside diameter of 6 French (0.079 inch/2.00 mm), and for optical fibers 2011 having a diameter of 0.155 mm.

As is conventional, the PA catheter 2001 has an inflatable balloon 2160 connected to a balloon inflation lumen 2004-1 which is coupled through the hub 2006 and flexible tubing 2007, to a balloon inflation/deflation port 2010-1. Another lumen 2004-6 provides for fluid injection or infusion through a fluid injection/infusion port 2010-6 for injection of fluid through an aperture 2012-6 located close to the sensor location P3. A central lumen 2004-7, which has an opening 2012-7 at the distal tip 2120, has an internal diameter which is sized to receive a standard guidewire, such as a 0.025 inch guidewire, to allow for over-the-guidewire directed insertion of the PA catheter. Thus, of the seven ports 2010-n (n=1 to 7), four of those ports 2010-2, 2010-3, 2010-4, 2010-5 comprise standard optical fiber connectors and the other three ports 2010-1, 2010-6 and 2010-7 are standard ports, such as luer fittings, i.e. for attachment of an air filled syringe for balloon inflation/deflation, for fluid injection or for guidewire insertion.

The positioning of the optical sensors 10, 20 within the catheter tubing 2002 is illustrated in more detail in the schematic longitudinal cross-sectional view shown in FIG. 6. There are three optical sensors 10, at sensor locations P1, P2 and P3, for measuring pressure and one optical sensor 20, at sensor location T, for measuring temperature. Each optical sensor 10 and 20 is optically coupled to a respective individual optical fiber 2011. That is, each optical sensor is integral with a sensor end of the fiber, or is bonded to the optical fiber, to provide an optical coupling of the sensor and fiber. Each optical fiber, carrying its sensor at the end, extends through its own individual lumen 2004-2, 2004-3, 2004-4, 2004-5 of the multi-lumen catheter, as illustrated in the transverse cross-sectional view in FIGS. 7 and 8, which are taken through plane A-A and B-B, respectively, of FIG. 6. The central lumen 2004-7 is sized to accept a guidewire, such as a standard 0.025 inch guidewire to facilitate insertion of the catheter. The other six lumens are arranged symmetrically around the central lumen. A first lumen 2004-1 and its port 2010-1 provides for balloon inflation, as is conventional, with a distal opening (2012-1 not visible) coupled to the balloon. The proximal port 2010-1 is coupled via the hub 2006 to lumen 2004-1 via a length of flexible tubing 2007, and the port 2010-1 is typically a luer type fitting for connection to an air filled syringe (2100 in FIG. 5) for inflation and deflation of the balloon 2160. Second, third and fourth lumens, i.e. lumens 2004-2, 2004-3, 2004-4, each accommodate one of the optical pressure sensors 10 and its optical fiber 2011. Each of these lumens have a respective distal aperture 2012-2, 2012-3, 2012-4, adjacent to the respective sensor locations P1, P2, P3 for fluid contact. A fifth lumen 2004-5 accommodates the optical temperature sensor 20 and its optical fiber 2011. At the proximal end, the optical fibers 2011 for each sensor extend through a length of flexible tubing 2008 from the hub 2006 to the respective optical connector 2010-2, 2010-3, 2010-4, 2010-5. Thus the fibers are protected within the flexible tubing 2008 to provide a flexible optical connection of a desired length for connection to the control system. The sixth lumen, 2004-6 is provided for fluid injection of a bolus of cold fluid, to allow for flow to be determined by thermo-dilution by detection of temperature changes by optical temperature sensor 20. This fluid injection lumen 2004-6 has a distal opening 2012-6 positioned for delivering fluid to the right atrium, i.e. approximately 30 cm from the distal tip 2120, close to the sensor position P3. When the sixth lumen is not being used for injectate for thermo-dilution measurements, it may alternatively be used for fluid infusion or injection for other purposes. As mentioned above, the central or seventh lumen 2004-7 is provided for a guidewire, if guidewire assisted insertion is required. After withdrawal of the guidewire, optionally this lumen may be used for other purposes, such as blood sampling at the tip of the PA catheter, e.g. for mixed venous oxygen saturation ($SvO_2$) measurements, or for measurement of cardiac output by the method of Fick.

As illustrated schematically in FIG. 6, the three optical pressure sensors 10 at sensor positions P1, P2, P3, and the optical temperature sensor 20 at position T, are provided along a length of the distal end portion 2130 spaced by distances $L_1$, $L_2$ and $L_3$ from sensor position P1. P1 is located at or close to the distal tip 2120, distal to the balloon 2160. P2 and P3 are arranged spaced apart lengthwise so that, in use, they can be located, respectively in the RV and the RA, when P1 is positioned in the PA. In use, corresponding apertures 2012-2, 2012-3, 2012-4 near each optical pressure sensor 10 allow for fluid contact with the optical pressure sensors. By way of example, P2 is located at a distance $L_2$ from P1, typically $L_2$ is about 20 cm; and P3 is located at a distance $L_3$ from P1, typically $L_3$ is about 30 cm. That is, the distance between P1 and P2, is about 20 cm and the distance between P2 and P3, is about 10 cm. The location of the optical temperature sensor T is proximal to the balloon and at a distance $L_1$ from P1, where $L_1$ is approximately 4 cm, so that the temperature sensor T is located in the PA when the pressure sensors locations P1, P2 and P3 are positioned, respectively, in the PA, the RV and the RA.

The transverse cross-sectional view shown in FIG. 7 through plane A-A of FIG. 6, illustrates the arrangement of the seven lumens of the catheter tubing of the catheter 2001 of this embodiment. There is a central lumen 2004-7 for a guidewire, e.g. of a suitable diameter to receive a standard 0.025 inch guidewire. As mentioned above, the central lumen may also be used for fluid injection or infusion, or for blood sampling. The other six lumens 2004-1 to 2004-6 are arranged symmetrically around the central guidewire lumen 2004-7. As mentioned above, three of the lumens accommodate the three pressure sensors 10 at locations P1, P2 and P3 and their optical fibers 2011. One of the lumens accommodates the temperature sensor 20 at location T and its optical fiber 2011. One lumen, for example 2004-1, is provided for balloon inflation. The other lumen, for example 2004-6, is provided for fluid injection or infusion. Thus, as shown schematically in the cross-sectional view in FIG. 8, through B-B of FIG. 6, an aperture or orifice 2012-4 is provided adjacent sensor P3 for fluid contact. Correspondingly, as shown in longitudinal cross-sectional view in FIG. 6, an aperture is also provided near each of the other pressure sensors 10 for fluid contact The lumen for fluid injection has an opening 2012-6 that is located proximal to the aperture 2012-4 for P3 by a short distance, e.g. by 1 cm, or a distance $L_4$, of about 31 cm from P1 at the distal tip 2120. The spacings of the three pressure sensors 10 are selected to allow sensor locations P2 to be placed in the RV and sensor location P3 to be placed in the RA when sensor P1 is in the PA, and so that the temperature sensor location T is positioned in the PA for measurement of blood flow in the PA by thermo-dilution.

Referring back to FIG. 5, the proximal part of the apparatus 2001 provides for optical coupling of the proximal end 2102 to the control unit 2151. Four of the proximal ports 2010-2, 2010-3, 2010-4 and 2010-5, for the four optical sensors (P1, P2, P3 and T), comprise a standard type of optical fiber connector, each of which connects to a corresponding optical input/output connector 2153 of the control unit 2151. The control unit 2151 houses a control system comprising a controller with appropriate functionality, e.g. including a processor, data storage, and optical source and optical detector, and it provides a user interface, e.g. a keypad 2154, and touch screen display 2152, suitable for tactile user input, and for graphical display of sensor data. The user interface connection 2155 (e.g. a standard USB cable, or alternatively, a wireless connection) is used to transfer data between the control unit 2151 to the touch screen display 2152. The control unit 2151 and touch screen display 2152 may optionally be integrated within a single housing or module. As illustrated schematically in FIG. 5, each of the optical sensors is connected by an individual optical connector to the control unit. Alternatively, in other embodiments, the proximal ends of the optical fibers for each of the optical sensors may be bundled together and coupled into a single multi-fiber proximal optical connector for connection to a multi-fiber optical port of the control unit. At the proximal end 2102 of apparatus 2001, a hub 2006 couples each lumen of the catheter via a respective length of flexible tubing to an individual proximal port. The other three ports, 2010-1, 2010-6 and 2010-7 comprise standard connections, such as Luer fittings, for attachment of a syringe or tubing. When not in use, the latter ports would typically be supplied with sterile plugs. In use, port 2010-1 is connected to a small air filled syringe 2100 for inflation/deflation of the balloon tip 2160. Port 2010-6 is used for fluid injection or infusion. Port 2010-7 is sized to accept a guidewire 2200, e.g. a standard 0.025 inch guidewire, or this port can be used for blood sampling at the tip of the catheter.

The optical pressure sensors 10 (P1, P2, P3) are preferably Fabry-Perot (FP) Micro-Opto-Mechanical System (MOMS) sensors, such as described by FISO Technologies (E. Pinet, "Pressure measurement with fiber-optic sensors: Commercial technologies and applications" 21st International Conference on Optical Fiber Sensors, edited by Wojtek J. Bock, Jacques Albert, Xiaoyi Bao, Proc. of SPIE Vol. 7753, (2011)). These optical pressure sensors comprise an optical fiber having a FP MOMS sensor at the sensor end of the fiber for sensing pressure. By way of example, for standard diameter optical fibers, each fiber (e.g., fibers 2011 in FIGS. 7 and 8) has a diameter of 0.155 mm (0.006 inch) and each optical pressure sensor (e.g., sensors 10 in FIG. 8) has a diameter of 0.260 mm (0.010 inch).

For measurement of flow by thermo-dilution, the optical temperature sensor 20 (T) may, for example, be a GaAs (Gallium Arsenide) fiber optic temperature sensor, as described by FISO technologies (E. Pinet et al., "Temperature fiber-optic point sensors: Commercial technologies and industrial applications", MIDEM Conference Proceedings, Sep. 29-Oct. 1, 2010, Radenci, Slovenia).

A typical material for fabrication of the multi-lumen catheter is a flexible polymer, such as, 4033 Pebax® (a Polyether block amide or PEBA, or other suitable thermoplastic elastomer (TPE)), which has regulatory approval for fabrication of conventional PA catheters. The wall thickness of the tubing may be ~0.005 inch. The guidewire lumen has a diameter, for example, of 0.029 inch to accommodate a standard 0.025 inch guidewire. Conventional coloring of the standard ports may be provided. A different color coding may be provided for the optical ports to facilitate quick recognition and connection to correspondingly color coded ports of the optical controller. As illustrated schematically the transverse cross-sectional views in FIGS. 7 and 8, sensors and fibers of these dimensions can be accommodated within catheter tubing 2002 having an outside diameter of 6 French (0.079 inch or 2.0 mm—see Table 1).

For some applications a larger diameter catheter, e.g. 7 French, may be acceptable.

For smaller fibers, e.g. 0.100 mm fibers, and smaller diameter sensors, if a guidewire lumen is not required, or if the guidewire to be used is smaller than 0.025 inch, e.g. 0.018 inch, the dimensions of the lumens and the outside diameter of the catheter tubing may be reduced in size accordingly, e.g. to 5 French or less.

It is preferable that the arrangement of the lumens has rotational symmetry about the longitudinal axis, and the wall thickness of each lumen is selected to provide the required mechanical characteristics, such as an appropriate degree of flexibility and stiffness, with symmetric torque characteristics along its length. For over the guidewire insertion, a more flexible catheter may be selected. For insertion without a guidewire, a stiffer catheter may be desirable. For example, while the catheter requires sufficient flexibility to traverse from the RA into the RV and then be guided into the PA, it is also desirable that the catheter has sufficient stiffness or rigidity (i.e. is not too floppy) to withstand turbulent blood flow within the ventricles, to withstand distortion or kinking, and to maintain a minimum bend radius of the optical fibers.

When the optical pressure sensors are FP MOMs sensors, they measure pressure at point locations of the sensor at the end of the fiber, i.e. pressure exerted on the FP membrane, and optical measurements are based on interference measurements, i.e. frequency shifts, rather than amplitude measurements. Blood pressure measurements are made with greater accuracy and reliability compared to conventional pressure sensing with a fluid filled catheter and an external pressure transducer. FP MOMS sensors can provide significantly more accurate pressure measurements, with minimal drift, compared to electrical pressure sensors, such as piezoelectric sensors. Optical pressure sensors avoid the need for multiple long thin electrical connections, which not only have significant electrical drift, but are subject to cross-talk and electro-magnetic interference. For similar reasons, it is also preferable that for measurement of flow by thermo-dilution or thermo-convection, the temperature sensor is preferably also an optical sensor rather than an electrical sensor. For example, for thermo-dilution measurements, the temperature sensor may be a fiber optic sensor which measures temperature based on the temperature dependence of a GaAs sensor at the tip of the fiber, i.e. a temperature dependent shift in the peak wavelength of light reflected from the sensor.

Figure 9:
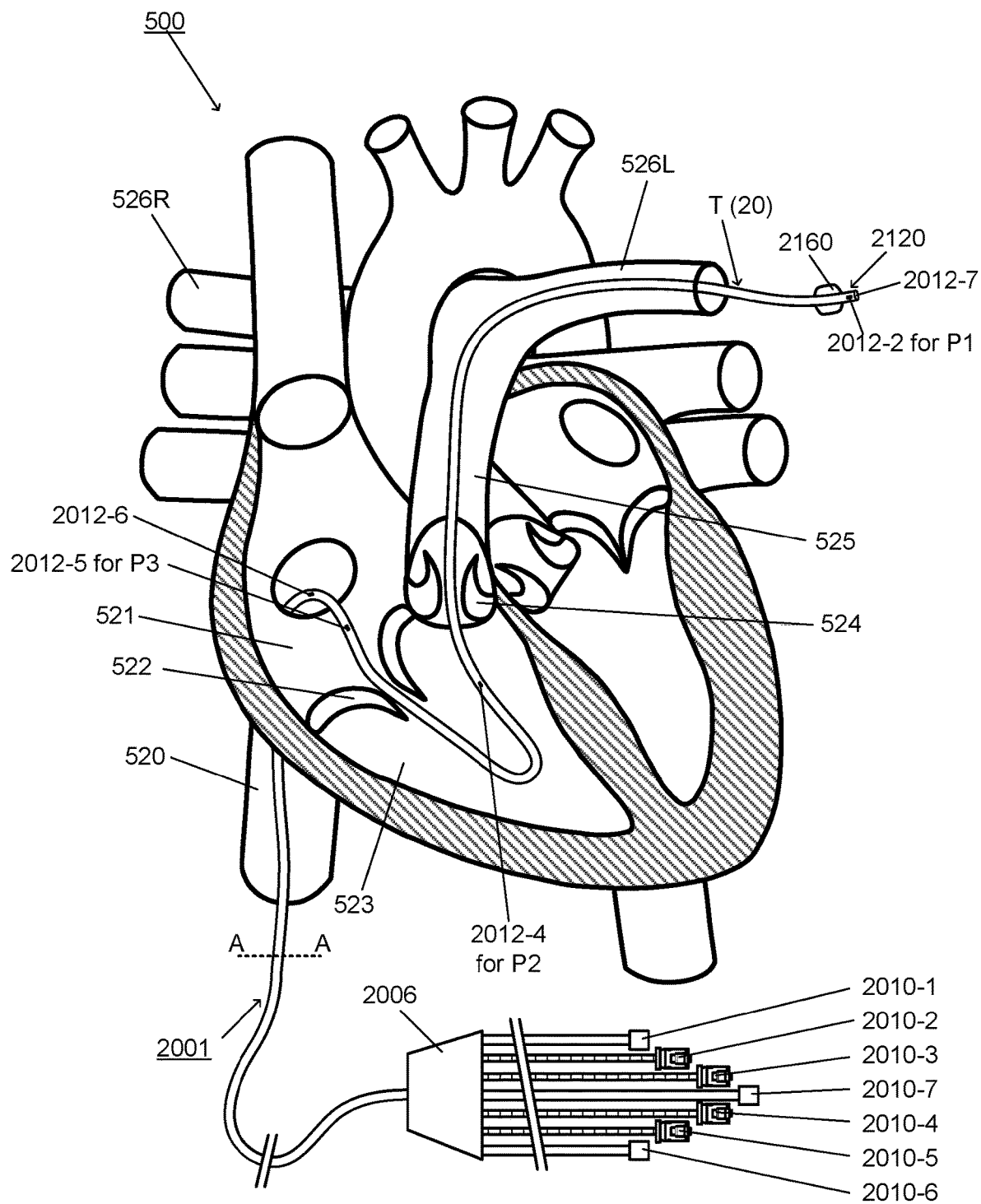
FIG. 9 shows a schematic partial cross-sectional diagram of a human heart to illustrate placement of the multi-sensor PA catheter of the first embodiment within the right heart and PA for diagnostic measurements of hemodynamic parameters, including concurrent measurements of blood pressure in the RA, in the RV, in the PA and the PCWP.

FIG. 9 provides a schematic diagram of the heart 500 to illustrate placement of the multi-sensor catheter 2001 of the first embodiment during a right heart and PA catheterization procedure to measure pressure concurrently in the right atrium 521, right ventricle 523 and PA 525. In this example, the multi-sensor catheter 2001 is introduced into the heart through the inferior vena cava 520, through the right atrium 521, through the tricuspid valve 522 into the right ventricle 523, through the pulmonic valve 524 and into the PA 525. The tip 2120 of the catheter extends into the left branch 526L of the PA. The aperture 2012-2 for pressure sensor P1, which is distal to the balloon 2160 is located in the left branch of the PA 526L. The temperature sensor T is also in the left branch of the PA 526L, proximal to the balloon. Aperture 2012-3 for pressure sensor P2 is located in the right ventricle 523. Aperture 2012-4 for pressure sensor P3 is located in the right atrium 521. The proximal fluid injection port 2012-6 is also located in the right atrium 521. Thus, when the optical connectors for the three optical pressure sensors P1, P2 and P3, and the optical temperature sensor T are connected to the optical control system, the pressure measurements in the RA, RV and PA can be made concurrently. Also, the optical temperature sensor T can be used for measurement of flow by a conventional thermo-dilution technique.

For some applications, a temperature sensor for measurement of flow by thermo-dilution may not be required, and it may be omitted.

Figure 10:
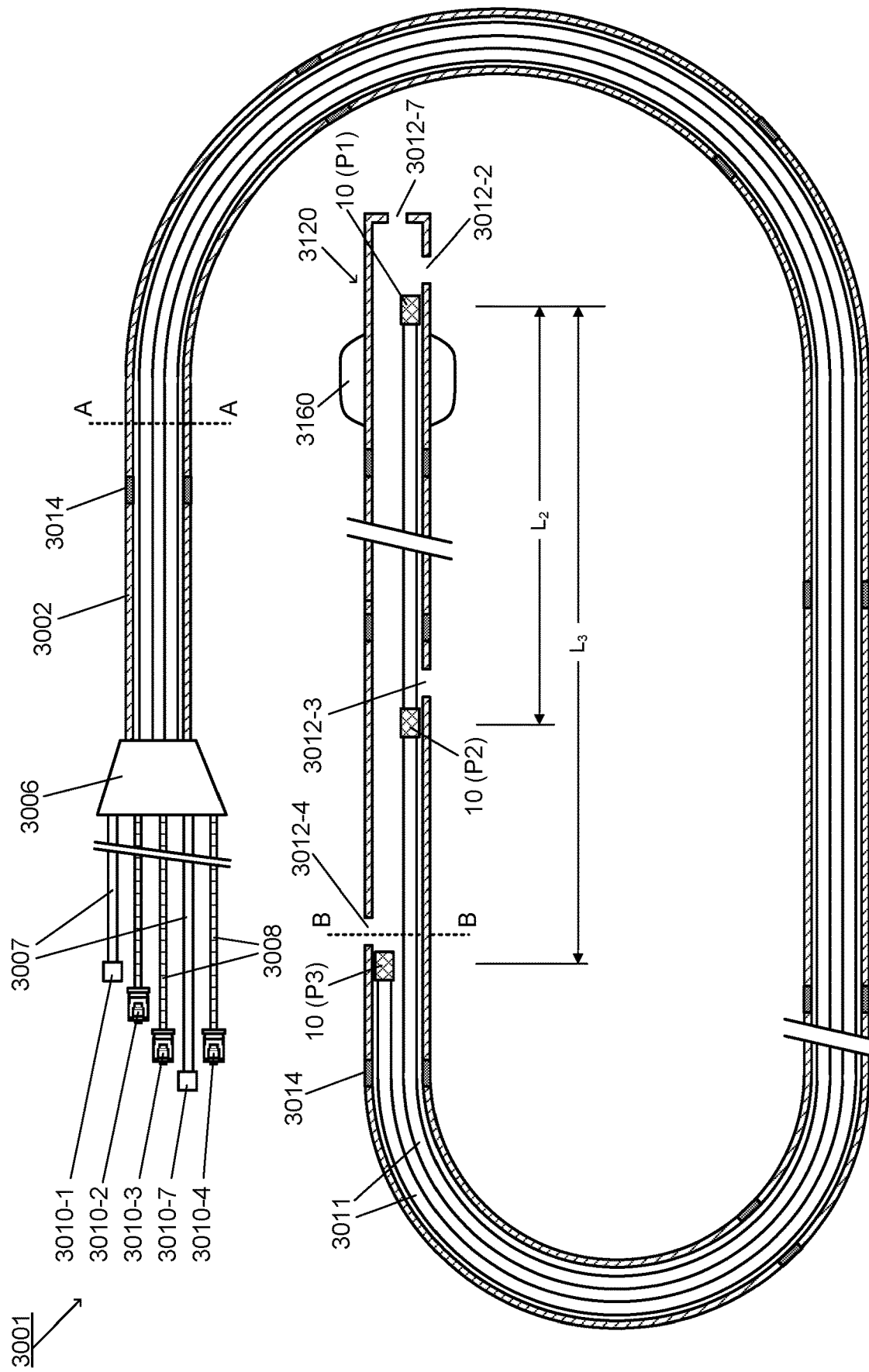
FIG. 10 shows a schematic longitudinal cross-sectional view of an apparatus for right heart and PA catheterization comprising a multi-sensor PA catheter according to the second embodiment of the present invention.
Figure 11:
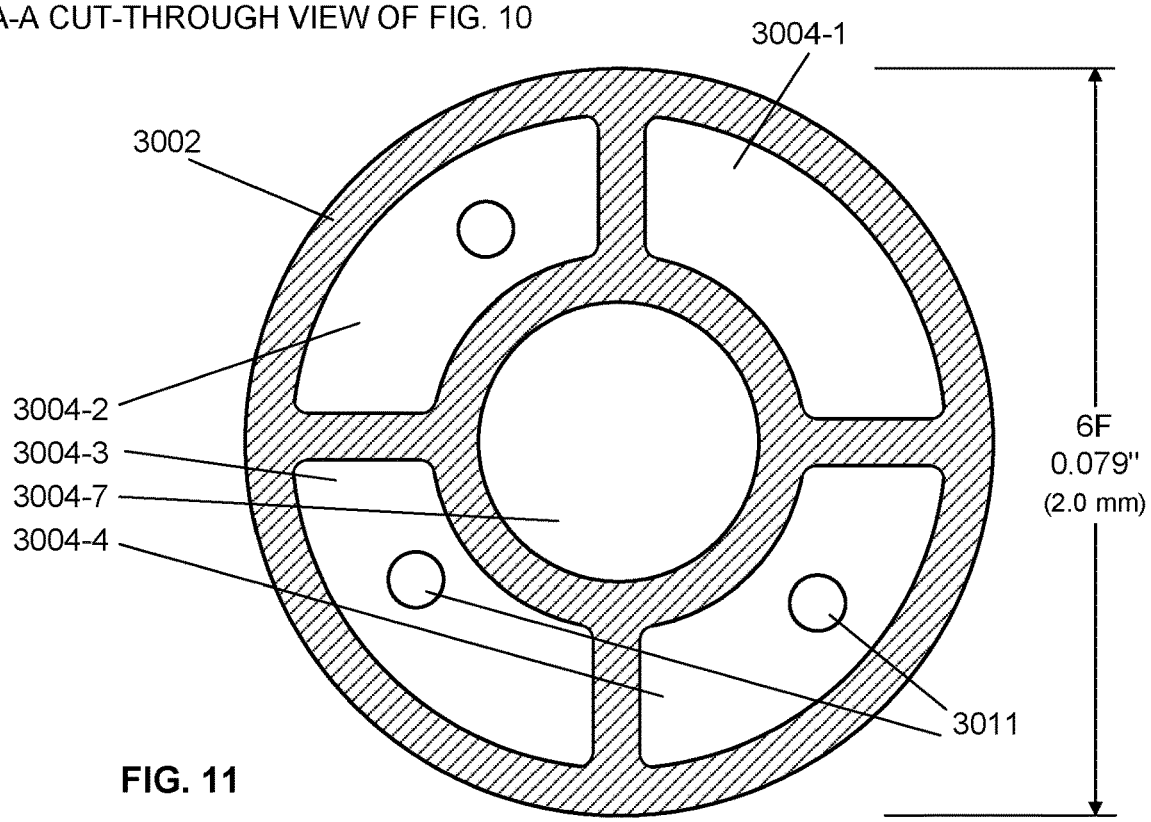
FIG. 11 shows an enlarged axial cross-sectional view of the multi-lumen catheter illustrated in FIG. 10 taken through plane A-A of FIG. 10.
Figure 12:
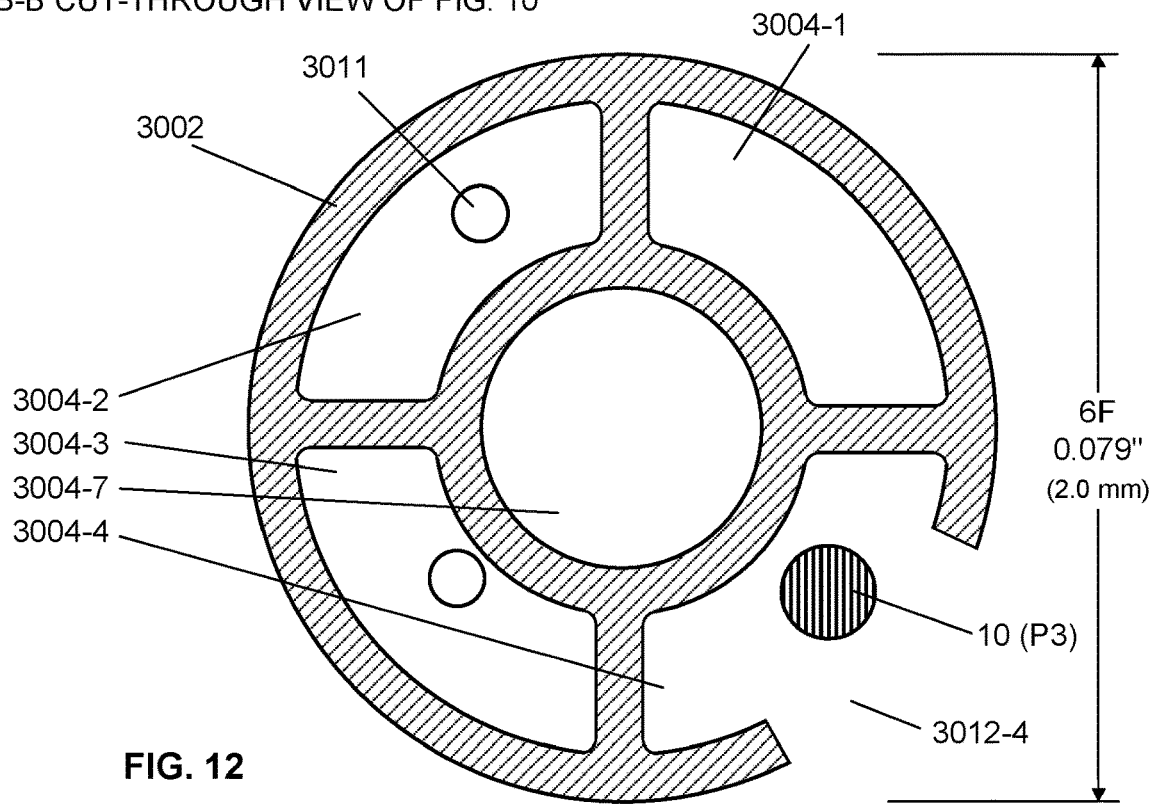
FIG. 12 shows an enlarged axial cross-sectional view of the multi-lumen catheter illustrated in FIG. 10 taken through plane B-B of FIG. 10.

A multi-sensor PA catheter 3001 of a second embodiment is illustrated in FIGS. 10, 11 and 12. As shown in a longitudinal cross-sectional view of FIG. 10, in this embodiment, the multi-sensor catheter comprises three optical pressure sensors 10, at sensor locations similar to those of the multi-sensor PA catheter 2001 of the first embodiment, but there is no temperature sensor. As illustrated in the transverse cross-sectional views in FIGS. 11 and 12, in this simplified version of the multi-sensor PA catheter, the catheter tubing 3002 comprises five lumens, i.e. a first lumen 3004-1 for balloon inflation; three lumens 3004-2, 3004-3, 3004-4, one for each of the three pressure sensors 10 and its respective optical fiber 3011; and the central lumen 3004-7 is provided for a guidewire, and/or for blood sampling, as described for the multi-sensor PA catheter of the first embodiment. As shown in FIG. 10, the optical fibers 3011 for the optical pressure sensors 10 are connected from the respective lumens, through connection hub 3006, and via flexible tubing 3008 to respective ports 3010-2, 3010-3 and 3010-4. Ports 3010-2, 3010-3, 3010-4 comprise optical connectors for the three optical pressure sensors 10 in the second, third and fourth lumens. Each of the three lumens 3004-2, 3004-3, 3004-4 has a respective aperture 3012-2, 3012-3 and 3012-4 for fluid contact with the respective optical pressure sensors 10. Port 3010-1 connects via tubing 3007 to the hub 3006 and the first lumen for inflation/deflation of the balloon 3160. Port 3010-7 connects via tubing 3007 to the central lumen which has an opening 3012-7 at the distal tip 3120 for a guidewire, or for blood sampling at the tip of the catheter. Radiopaque markers 3014 are provided along the length of the catheter tubing to assist in positioning the sensors 10 within the heart. As illustrated, by way of example, in FIGS. 11 and 12, the catheter tubing has an external diameter of 6 French, and provides a central lumen 3004-7 having an inside diameter which can accept a guidewire, e.g. a standard 0.025 inch guidewire, and four lumens arranged symmetrically around the central lumen. That is, one lumen for balloon inflation, and three lumens for three optical fibers of 0.155 mm diameter and FP-MOMS optical pressure sensors of 0.260 mm diameter. The outside diameter of the PA catheter tubing may be reduced if smaller diameter optical fibers and sensors are used, or for use with a smaller diameter guidewire.

In comparing the multi-sensor catheters of the first and second embodiments, comprising 7 lumens and 5 lumens respectively, it will be appreciated that the dimensions of each catheters, such as the external diameter, the number of lumens and the thicknesses of the internal walls of the catheter defining each lumen are described by way of example only. As mentioned above, smaller optical sensors and smaller optical fibers may be accommodated within smaller lumens, to provide a catheter having a smaller outside diameter. This may be desirable for some applications. The material from which the catheter is made, and the wall thicknesses defining the lumens, may be selected to provide the catheter with a required stiffness or flexibility, and size.

In other alternative embodiments, when the catheter is to be flow directed by the balloon tip, and introduction over a guidewire is not required, the guidewire lumen may be omitted.

For some applications, for example for pediatric or neonatal use, a significantly smaller diameter catheter may be required, e.g. 3 French. Correspondingly, the spacings of the optical pressure sensors would be closer together, i.e. matched to the smaller dimensions of the chambers of patient's heart, for placement of one sensor in the RA, one in the RV and one in the PA. In such a case the guidewire lumen may be omitted so that three pressure sensors can be accommodated within a multi-lumen catheter of the required diameter. While three pressure sensors are desirable for concurrent measurements of RA, RV and PA pressure waveforms, when a guidewire lumen is required for a smaller diameter catheter, it may only be possible to accommodate two optical pressure sensors. In this arrangement, the two sensors would be spaced apart so that initially, one sensor can be positioned in the RA and one in the RV for concurrent measurement of RA and RV pressure waveforms, and then subsequently the catheter would be advanced to position one sensor in the RV and one in the PA for concurrent measurement of RV and PA pressure waveforms, and for RV and PCWP pressure waveforms.

The lengthwise spacings ($L_2$ and $L_3$) of the optical pressure sensors at locations P1, P2 and P3 described with respect to the multi-sensor catheters of the first and second embodiments, i.e. for measurement of pressure waveforms concurrently in the RA, RV and PA refer to typical spacings required for an adult human heart, where the distance from the RA to the RV is about 10 cm and the distance from the RV to the PA, in a region downstream of the pulmonic valve, is about 10 cm. The PCWP position is typically a further 10 cm into one of the right or left branches of the pulmonary artery, i.e. about 20 cm from the RV. Thus, to position P1 in the PA near the wedge position, P2 in the RV, and P3 in the RA, $L_2$ is about 20 cm and $L_3$ is about 30 cm. The location of the temperature sensor T is typically positioned between P1 and P2, spaced a distance $L_1$ from P1, for measurement of blood flow within the PA, where $L_1$ is e.g. about 4 cm to 10 cm. For pediatric and neonatal use, i.e. for smaller sized hearts, the spacings of the sensors would be reduced accordingly.

While it is envisaged that multi-sensor catheters for right heart and PA catheterization may comprise more than three optical pressure sensors, there is a practical limit to how many sensors can be accommodated within a multi-lumen catheter of a particular outside diameter.

Since multi-sensor PA catheters are intended as disposable, single use catheters, in practice, the number of optical sensors may also be limited by component costs and fabrication costs. Currently, standard diameter optical fibers and optical pressure sensors are lower cost than smaller diameter optical fibers and optical pressure sensors. Since each pressure sensor is in an individual lumen of the multi-lumen catheter, the available space for each lumen is also limited by the wall thickness and tolerances for each lumen of a multi-lumen catheter. As described herein, it is currently feasible to manufacture a multi-sensor PA catheter with three optical pressure sensors and one optical temperature sensor, within a 6 French multi-lumen catheter. Use of smaller fibers and sensors or smaller guidewire may allow the diameter to be reduced to 5 French or less.

In a multi-sensor catheter of yet another embodiment, instead of three optical pressures sensors and one optical temperature sensor, it may be desirable to have four optical pressure sensors to enable concurrent pressure measurements in the right atrium, in the right ventricle, in the PA near the pulmonic valve and also in a branch of PA for measurement of the PCWP.

For example, if a temperature sensor is not required for blood flow measurements, for example where blood flow is measured by an alternative technique, e.g. by the Fick method, a fourth optical pressure sensor may be provided instead of the optical temperature sensor, so that the multi-sensor catheter can be introduced so as to position one sensor in the RA, one sensor in the RV, one sensor in the PA, and one sensor for measuring PCWP when the balloon is inflated. By way of example, in such an arrangement, four pressure sensors P1, P2, P3 and P4 are spaced at intervals of ~10 cm, i.e. the distance P1 to P2 ($L_1$) is 10 cm, P1 to P3 ($L_2$) is 20 cm, and P1 to P4 ($L_3$) is 30 cm.

This arrangement may be desirable for longer term monitoring of pressure waveforms in the RA, RV, PA, as well PCWP pressure waveforms. That is the catheter may be positioned in a fixed and stable location, to enable observation of pressure waveforms at each sensor location over an extended time period, e.g. for ICU patients requiring monitoring over several days or more.

Alternatively, where it is not feasible to accommodate an optical temperature sensor as well as the desired number of optical pressure sensors, or for cost reasons, a conventional small sized, low cost, electrical flow sensor, i.e. a thermistor, may be used, with conventional electrical connections to the control system.

In the embodiments described above, radiopaque markers may be provided near the balloon, and optionally near each sensor, to assist in locating the tip and positioning the sensors in use, i.e. using conventional radio-imaging techniques, when introducing the guidewire and positioning the pressure sensors in the right atrium, right ventricle and PA. The radiopaque markers typically comprise a suitable heavy metal e.g. barium, tantalum, gold or platinum. Alternatively, markers are provided at regular intervals, e.g. at 10 cm intervals along the length of the catheter tubing as is conventional for PA catheters.

Preferably that the optical fibers have some freedom to move or slide within the lumen when the catheter is flexed. The fibers are of the appropriate length so that the sensors at the sensor end (distal end) of the fibers are appropriately positioned at sensor locations in the distal end portion of the catheter. Each of fibers may be secured near the proximal end, e.g. by adhesive bonding where they pass through the hub. Each fiber may also be secured in its lumen, near the sensor location, e.g. by injection of a medical grade adhesive through the wall of the lumen.

If required, in use, the lumens containing the fibers and sensors may be flushed with fluid, e.g. saline solution, to remove air from the catheter lumens. Alternatively, an adhesive, or a medical grade gel, may serve to plug the lumen each side of the aperture surrounding the optical sensor, while leaving the sensor exposed for fluid contact. For example, a bolus of medical grade adhesive may be injected through the tubing to secure the fiber near each sensor and to plug the lumen around the fiber. Similarly, the adhesive may also be injected into the lumen distal to the aperture. Also, if required, components of the multi-sensor catheter may be coated to reduce blood clotting, for example, if the multi-sensor catheter is to be left in place for an extended period.

The optical pressure sensors 10 at locations P1, P2, P3 are preferably Fabry-Perot Micro-Opto-Mechanical-Systems (FP MOMS) pressure sensors. As an example, a suitable commercially available FP MOMS pressure sensor is the Fiso FOP-M260. These FP MOMS sensors meet specifications for an appropriate pressure range and sensitivity for blood pressure measurements. They have an outside diameter of 0.260 mm (260 µm). Typically, they would be attached and optically coupled (i.e. integral with or bonded to) to a sensor end of an optical fiber with an outside diameter of 0.100 mm (100 µm) to 0.155 mm (155 µm). Optical fibers and FP MOMS sensors of smaller diameter tend to be more expensive, and may be used, when appropriate.

The optional optical flow sensor 20 may comprise an optical thermo-dilution or an optical thermo-convection flow sensor, e.g. as described in U.S. patent application Ser. No. 14/354,588.

For operation of the optical sensors, the optical output ports 2010-2, 2010-3, 2010-4, 2012-5 couple to the respective optical ports of the control unit 2151 (e.g. see FIG. 5) for controlling operation of the optical sensors 10 and 20. The flexible tubing 2008 surrounding each of the optical fibers extends between the hub 2006 and the optical connector of the control unit to provide a flexible optical coupling from the hub 2006 to the control unit 2151. This tubing is provided to protect the optical fibers and can have any appropriate diameter and flexibility. Since the catheter is intended for single use only, preferably the optical connectors are standard low cost optical connectors. Similarly, the flexible tubing, and other connectors for the other ports are preferably standard materials and components, such as luer fittings or other medical standard fluid ports and electrical connectors, as appropriate, which can be sterilized, and so that the multi-sensor catheters can be provided in single-use sterile packaging, using conventional standard processes for medical devices.

For protection of the sensors during assembly, it may be preferred to insert optical fibers and optical sensors through the respective lumen from the distal end of the catheter and subsequently form the optical connector at the proximal end, and then close the lumen at the distal tip. On the other hand, when the optical connector is pre-formed at the proximal end of the sub-assembly before insertion, the sensor end of the sub-assembly is inserted into the catheter from proximal end of the respective lumen. In either case, it is preferable that the catheter lumens have smooth rounded surfaces, with non-stick internal surfaces, i.e. to avoid sharp edges, so that the sensors and optical fibers can slide smoothly into their catheter lumen without catching on sharp edges or corners, to avoid mechanical damage to the sensors or optical fibers. However, in use of the multi-sensor catheter, it is preferable that the fibers are fixed at the proximal end only of the catheter tubing so that the fibers have some freedom to move or slide within the lumens when the catheter is flexed. If required, the optical fibers may also be adhesively bonded near the aperture to secure the sensor at the appropriate sensor location.

As mentioned above, it is desirable that the multi-sensor PA catheter has mechanical characteristics, such as stiffness and flexibility, similar to a standard PA catheter. The optical fibers and optical sensors do not add significant stiffness to the catheter, and thus these characteristics are primarily determined by the type of material and wall thickness used for the multi-lumen catheter tubing.

Other factors for consideration are: regulatory requirements for medical devices, ease of use and safety. For these reasons, it is desirable that the materials for fabrication of a multi-sensor PA catheter are based on a conventional tried and tested PA catheter or other medical device, i.e. based on a predicate device structure which has regulatory approval and which is fabricated with materials and components which already have FDA and/or CE mark regulatory approval.

It will be appreciated that in alternative embodiments or variants of the multi-sensor catheters of the embodiments described in detail above, different combinations of one or more features disclosed herein, and features disclosed in the related patent applications referenced herein, may provide multi-sensor catheters of further alternative embodiments As disclosed herein, the cardiologist is offered multi-sensor catheters which have particular application for right heart and PA catheterization. These multi-sensor catheters are configured for monitoring and diagnostic measurements of hemodynamic parameters, including concurrent measurement of blood pressure within the RA, RV and PA.

Control System and Graphical Display of Pressure Waveforms and Associated Hemodynamic Parameters.

Figure 13A:
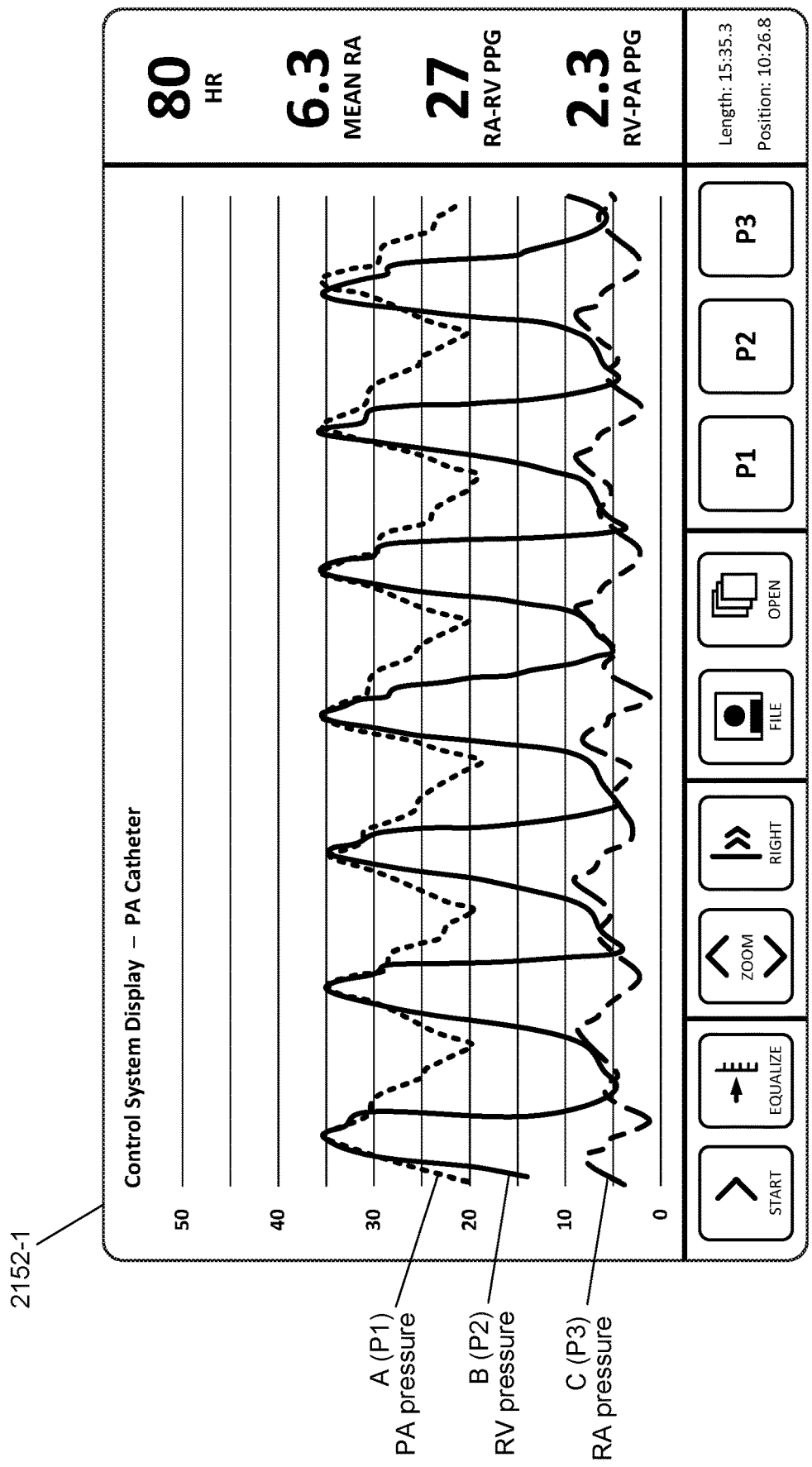
FIG. 13A illustrates schematically a graphical display of the control system showing three concurrent blood pressure waveforms from: A. sensor position P1 in the pulmonary artery (balloon deflated); B. sensor position P2 in the right ventricle; and C. sensor position P3 in the right atrium; together with selected numeric data comprising hemodynamic parameters derived from the pressure waveforms.
Figure 13B:
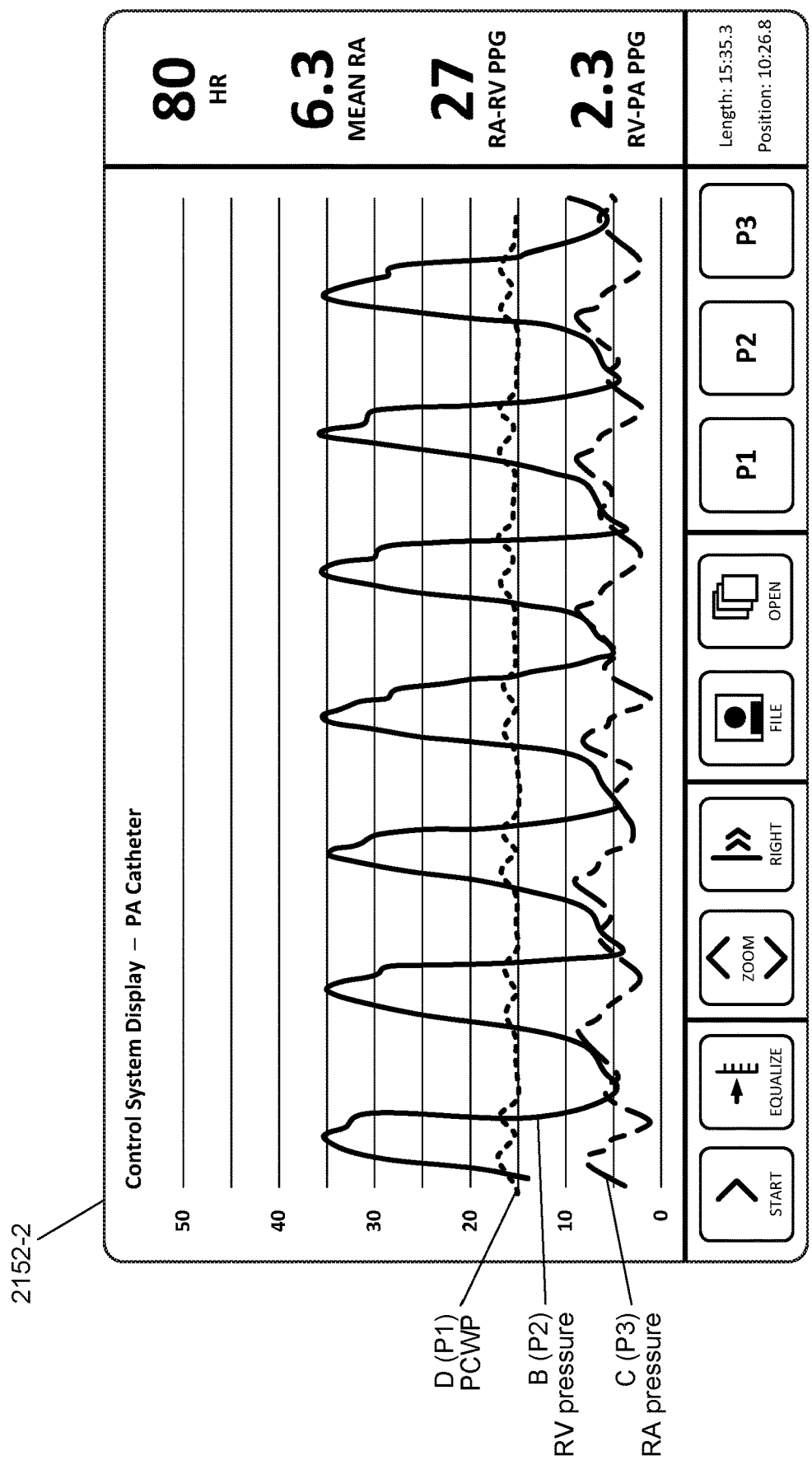
FIG. 13B illustrates schematically a graphical display of the control system showing three concurrent blood pressure waveforms from: D. sensor position P1 in the pulmonary capillary wedge position with the balloon inflated; B. sensor position P2 in the right ventricle; and C. sensor position P3 in the right atrium; together with selected numeric data comprising hemodynamic parameters derived from the pressure waveforms.
Figure 14:
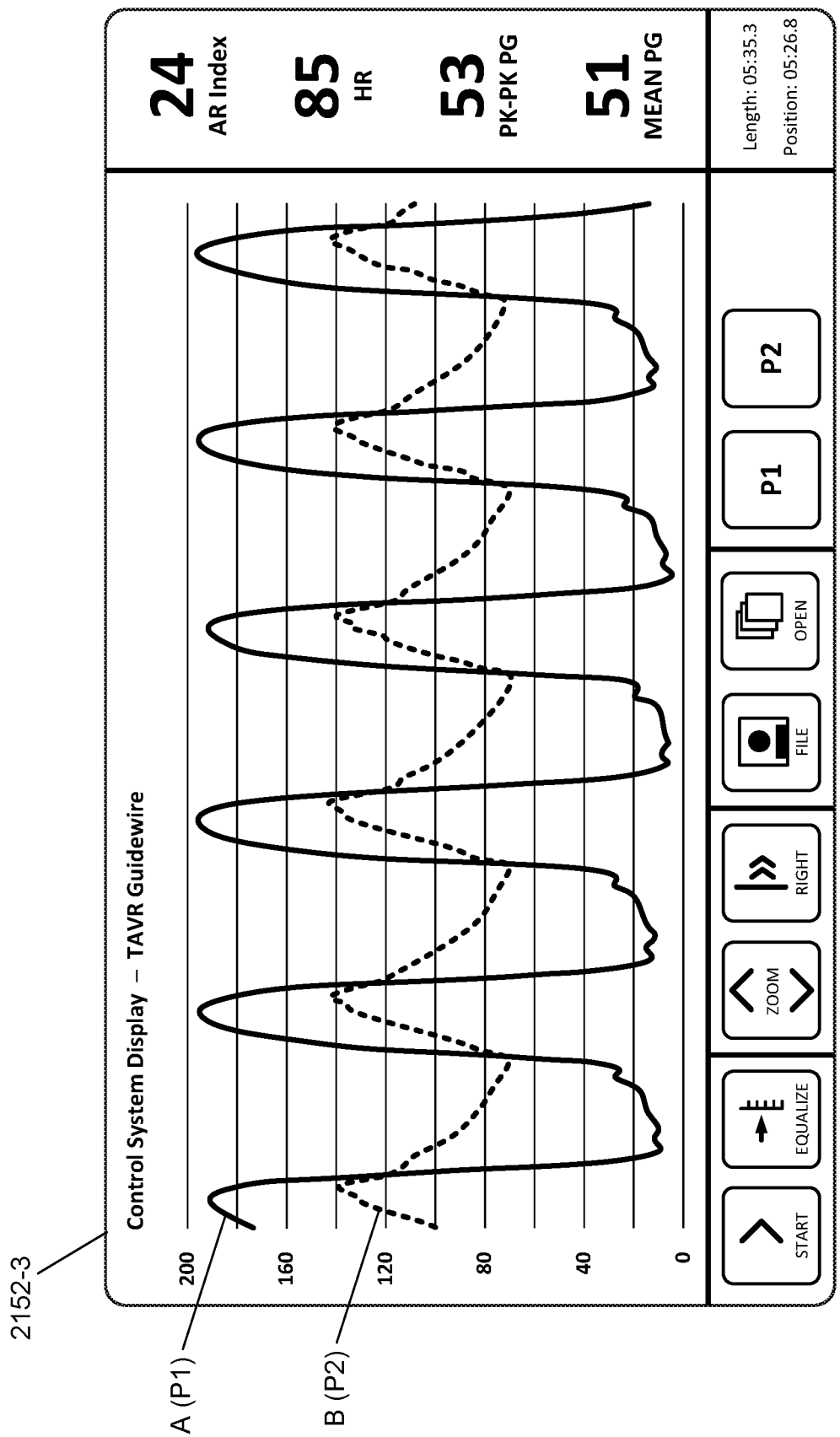
FIG. 14 illustrates schematically a graphical display of the control system showing concurrent pressure waveforms from: A. sensor position P1 in the aorta and B. sensor position P2 in the right ventricle, with numeric data comprising hemodynamic parameters derived from the pressure waveforms, including an aortic regurgitation index (AR Index).

Referring to the control system, which was described above with reference to FIG. 5, and as described in the above referenced related patent applications, it will be apparent that the control system may be used with multi-sensor catheters and multi-sensor guidewires for concurrent blood pressure measurements at each pressure sensor location, using, two, three or more optical pressure sensors. Optionally, for flow measurements, the multi-sensor catheter or guidewire is further equipped with an optical or electrical flow sensor. The control system comprises a light source and detector and an optical interface for coupling, via respective input/output ports, to each of the optical fibers and optical sensors of the multi-sensor catheter or guidewire. The control system also comprises data storage and processing means configured for processing optical data indicative of pressure values and optionally, optical or electrical data indicative of flow velocity values. For use with multi-sensor catheters and multi-sensor guidewires, for example, the multi-sensor catheter disclosed herein having three optical pressure sensors, and an optional optical flow sensor, the control system would have a corresponding number of signal processing channels with optical inputs for each of the optical sensors. The signal processing elements for each channel may be referred to as a signal conditioning unit. For measuring blood pressure and flow within the heart and blood vessels, in particular for measuring intravascular or transvalvular blood pressure gradients, the processing means is further configured for graphically displaying pressure data, and optionally flow velocity data, comprising a plurality of blood pressure waveforms, i.e. a pressure waveform from each optical pressure sensor. The concurrent blood pressure waveforms for each of the optical sensors may be displayed for one or more time intervals, and during one or more cardiac cycles. Preferably, the processing means is further configured to derive hemodynamic parameters from the blood pressure data, and optionally from flow velocity data, and display numeric values of the parameters as well as display the pressure waveforms from each sensor. By way of example only, some schematic representations of pressure waveforms and associated numeric data, for a patient with a healthy or normally functioning heart, are shown in FIGS. 13A, 13B and 14. In practice, pressure waveforms and pressure values vary from patient to patient and may be dependent on a number of factors, such as, whether or not the patient has a healthy or diseased heart, or other conditions that may affect functioning of the heart. Skilled medical practitioners will recognize characteristic variations in each pressure waveform and associated pressure values, indicative of e.g. valvular stenosis or other patient physiology. Advantageously, in use of a multi-sensor catheter, concurrent pressure measurements from multiple optical pressure sensors enable the cardiologist to directly compare multiple pressure waveforms, in real-time, from the RA, RV and PA/PCWP.

As an example, FIG. 13A represents a graphical display 2152-1 showing three blood pressure waveforms from a three sensor PA catheter: A. pressure sensor location P1 in the pulmonary artery; B. pressure sensor location P2 in the right ventricle; and C. pressure sensor location P3 in the right atrium. Pressure units are displayed in mmHg. Optionally, it may be desirable to select and display one or multiple pressure waveforms and related parameters in different formats. For example, during right heart and pulmonary artery catheterization with a multi-sensor catheter as disclosed herein, in addition to displaying concurrent blood pressure waveforms from each the right atrium, right ventricle and pulmonary artery, a plurality of numeric values, such as, peak pressures, mean pressures, peak-to-peak (PK-PK) pressure differentials for each curve, and pressure differentials or gradients between the right atrium and right ventricle, and between the right ventricle and pulmonary artery may be displayed in real time. For example, as illustrated schematically by the numeric data to the right of the graphical display shown in FIG. 13A, numeric data selected for display may include the mean pressure of the RA, systolic/diastolic pressure for RV/PA, a peak-to-peak gradient (PPG) for RV to PA, a PPG for RA to RV, and heart rate HR. As is conventional, the user interface may include a number of buttons or keys, such as shown at the bottom of the display in FIG. 13A, e.g. to select parameters for display, change display modes, and input identification. FIG. 13B represents a graphical display 2152-2 for three pressure waveforms, similar to that shown in FIG. 13A, except that waveform A for the PA pressure is replaced with waveform D for the pressure sensor location P1 is in the pulmonary capillary wedge position with the balloon inflated.

Correspondingly, in use of a multi-sensor guidewire during TAVR, e.g. a multi-sensor guidewire with two optical pressure sensors to assess functioning of the aortic valve, before and after a TAVR procedure. As illustrated schematically in FIG. 14, the system comprises a graphical display 2052-3 which shows two pressure waveforms: A. from pressure sensor location P1 in the left ventricle and B. from pressure sensor location P2 in the aorta, together with numeric values derived from the pressure waveforms from the left ventricle and aorta, e.g. a transvalvular pressure gradient. For example, the system may automatically compute an aortic regurgitation index (ARi or AR Index) and display the ARi value in real time. The ARi may be computed from measured values of the left ventricular end-diastolic pressure (LVEDP), diastolic blood pressure (DBP), and systolic blood pressure (SBP), as illustrated in FIG. 14. and is defined as:

$$ARi=((DBP-LVEDP)/SBP)\times 100$$

In one embodiment, the control system comprises a signal processing unit for receiving optical data and optionally electrical data, from a multi-sensor catheter or guidewire. The signal processing unit is coupled by a data connection to a general purpose computer system, which may be personal computer (PC), such as a laptop or tablet PC, comprising processing means, i.e. one or more processors and a computer program product, embodied in a non-transitory computer readable medium storing instructions, in the form of code, for execution by the processing means. The computer program product is, for example, a software application comprising instructions for execution in a processor of the tablet PC for receiving or retrieving data, and displaying a plurality of concurrent pressure waveforms from the optical pressure sensors, and for computing, and displaying in real-time, associated hemodynamic parameters or an index, such as ARi.

In another example of a TVT procedure, a multi-sensor guidewire or catheter may be used for measurement of concurrent pressure waveforms upstream and downstream of the mitral valve, e.g. to assess functioning of the mitral valve before and after TMVI.

For example, the tablet PC is configured for graphically displaying pressure data, and optionally flow velocity data, e.g. comprising a plurality of blood pressure waveforms. The concurrent blood pressure waveforms for each optical sensor may be displayed for one or more time intervals, and during one or more cardiac cycles. The processing means is further configured to derive and display hemodynamic parameters from the blood pressure data and flow velocity data. For example, during right heart and pulmonary artery catheterization with a multi-sensor catheter as disclosed herein, in addition to displaying blood pressure waveforms from the right atrium, right ventricle and pulmonary artery, a selected plurality of numeric values such as peak pressures, mean pressures, peak to peak pressure differentials for each curve, and pressure differentials or gradients between the right atrium and right ventricle, and between the right ventricle and pulmonary artery can be displayed in real time.

As is conventional, the system may comprise a user interface, such as a keyboard or touchscreen, to allow the operator to select from available information which waveforms or parameters are to be displayed. The interface may allow the operator to input user data such as patient identification, and data interfaces may be provide to output data to other devices or systems, or receive data from other sources, such as from other sensors or monitoring systems, which are typically used in an ICU or OR. For example, in a cardiac catheterization laboratory, the control system for a multi-sensor catheter or guidewire may be coupled to, or part of, a computing system controlling other equipment, and which is equipped with one or more large screen displays close to the operating table, and other remote displays in a monitoring area. The latter are used to display various forms of data, sequentially, concurrently, or on demand. Such data may include, e.g. fluoroscopic imaging, with or without contrast media, and transesophageal echo-cardiography (TEE) images, as well as sensor data comprising pressure waveforms from the multi-sensor catheter or guidewire and associated hemodynamic parameters calculated or derived from the received optical pressure sensor data.

While a specialized signal processing unit or interface, which may be referred to as a "signal conditioner", is used to receive optical data from the multi-sensor catheter or multi-sensor guidewire, and generate output data indicative of pressure for display of pressure waveforms, the output data may be fed by a standard data connection, wired or wireless, to a processor, such as a general purpose computer, which is configured to provide the required functionality. For example, the system includes a processor and a computer program product (typically referred to as a software application or computer code), embodied in a non-transitory computer readable medium storing instructions, for execution in a processor of a control system for a multi-sensor catheter or a multi-sensor guidewire, for processing optical data received concurrently from a plurality of optical pressure sensors indicative of blood pressure, displaying a corresponding plurality of blood pressure waveforms, and optionally flow velocity data, and displaying numeric data relating to selected hemodynamic parameters and indexes.

TABLE 2

| | Abbreviations or acronyms |
|---|---|
| ARi or AR Index | Aortic Regurgitation Index |
| Cath Lab | Cardiac Catheterization Laboratory |
| CO | Cardiac Output |
| CVC | Central Venous Pressure catheter |
| DBP | Diastolic Blood Pressure |
| FP MOMS Sensor | Fabry-Pérot Micro-Opto-Mechanical-System Sensor |
| ICU | Intensive Care Unit |
| LAP | Left Atrial Pressure |
| LVEDP | Left Ventricular End-Diastolic Pressure |
| OR | Operating Room |
| PA | Pulmonary Artery |
| PCWP | Pulmonary Capillary Wedge Position/Pressure |
| PEBA | PolyEther Block Amide |
| RA | Right Atrium |
| RHC | Right Heart Catheterization |
| RV | Right Ventricle |
| $SvO_2$ | Mixed venous oxygen saturation |
| SBP | Systolic Blood Pressure |
| TAVI or TAVR | Transcatheter Aortic Valve Implantation or Replacement |
| TMVI or TMVR | Transcatheter Mitral Valve Implantation or Replacement |
| TPE | Thermoplastic elastomer |
| TVR | Transcatheter heart Valve Replacement |
| TVT | Transcatheter Valve Therapies (TVT). |

INDUSTRIAL APPLICABILITY

Multi-sensor PA catheters according to embodiments of the invention disclosed herein provide real-time, concurrent, multi-chamber (RA and RV) pressure measurements within the right heart and also the PA. Each pressure measurement is taken concurrently under identical and stable conditions, while the multi-sensor catheter is positioned to locate one sensor in each of the RA, RV and PA.

In contrast, during RHC using a conventional PA catheter, it is necessary to move the catheter to get each pressure measurement, so each measurement is taken at a different time, under different conditions. For example, withdrawing a PA catheter from the PA to the RV may cause cardiac arrythmia or premature ventricular contraction (PVC). That is, the instantaneous condition for each pressure measurement is impacted by moving the catheter.

In some instances, such as monitoring in an ICU, it may be too risky to move the PA catheter once the catheter tip is placed in the PA. For a conventional PA catheter, it would then only provide the PA pressure, not a RV and RA pressure. Thus, where appropriate, the multi-sensor catheter offers continuous real-time and concurrent monitoring of all of RA, RV and PA pressures for an extended time, e.g. over a period of days, for an ICU patient. In this scenario, RA pressure monitoring provides alternative to monitoring of central venous pressure (CVP).

For post-operative monitoring, there may be risks in use of a Swan Ganz catheter, and there is a need to appropriately select patients who need Swan Ganz catheterization. For patients where Swan Ganz catheterization is appropriate, the multi-sensor PA catheter offers continuous real-time and concurrent monitoring of all of RA, RV and PA pressures.

Since these pressure measurements also provide an indirect measure of left heart hemodynamic parameters, these measurements can help to identify pathology and physiological problems and select appropriate therapies, drugs, and procedures. For example, pressure measurements may help to differentiate patient physiologies, and identify a filling problem vs. a valve problem, such as, an obstruction of the tricuspid valve.

For example, multiple concurrent blood pressure measurements during RHC may show, e.g., a high RA pressure and a low RV pressure, which may indicate tricuspid valve stenosis/obstruction. In conditions such as pulmonary edema, concurrent pressure measurements of the RA, RV, PA and PCWP may provide information which helps to determine or differentiate, e.g., whether is symptoms are caused by a RH or LH problem, a valve problem (stenosis or regurgitation), a muscle problem, cardiac restriction or constriction, PA hypertension, or a primary lung problem (such as Acute Respiratory Distress Syndrome).

The number of TAVR procedures per year is projected to increase dramatically in the next few years. During left heart catheterization for TAVR, the Aortic Regurgitation index (ARi) is a widely used parameter for assessing function of the aortic valve before and after valve repair or replacement. It is also expected that the mitral valve replacement will increase in future years, but aortic valve replacement is much more common.

By comparison, pulmonic valve interventions are rare and there is not a commonly used PA index. However, multi-sensor catheters providing concurrent pressure measurements in the RA, RV and PA may allow for an appropriate index to be adopted for RHC.

Although embodiments of the invention have been described and illustrated in detail, it is to be clearly understood that the same is by way of illustration and example only and not to be taken by way of limitation, the scope of the present invention being limited only by the appended claims.

The invention claimed is:

1. A multi-sensor catheter for direct measurement of blood pressure during cardiac catheterization comprising:
 a length of catheter tubing comprising a plurality of lumens extending between a proximal end and a distal end, and the distal end comprising a distal tip;
 a plurality of optical sensors and a plurality of optical fibers; a sensor end of each optical fiber being attached and optically coupled to an individual one of the plurality of optical sensors;
 the plurality of optical sensors and optical fibers being inserted into the plurality of lumens, the sensor ends of each optical fiber being spaced apart lengthwise to provide a sensor arrangement with said plurality of optical sensors positioned at respective sensor locations within a distal end portion of the catheter tubing;
 a proximal end of each of the plurality of optical fibers being coupled to an optical input/output connector at the proximal end of the multi-sensor catheter for connection to an optical control system; and
 the plurality of optical sensors of the sensor arrangement comprising at least two optical pressure sensors, with an aperture in the catheter tubing adjacent each optical pressure sensor for fluid contact; and
 wherein the sensor locations are configured to enable positioning of the at least two optical pressure sensors at positions within chambers of the heart, aorta and pulmonary artery comprising one of:
  a) right atrium and pulmonary artery;
  b) right atrium and right ventricle;
  c) left ventricle and left atrium;
  d) right atrium and left atrium;
  e) aorta and left ventricle; and
  f) right ventricle and pulmonary artery,
 to provide concurrent measurements of blood pressure waveforms by said at least two optical pressure sensors as positioned during cardiac catheterization.

2. The multi-sensor catheter of claim 1, having an outside diameter sized to allow insertion through a vein in an upper or lower arm.

3. The multi-sensor catheter of claim 1, comprising an inflatable balloon near the distal tip, the inflatable balloon being coupled by a balloon inflation lumen of the catheter tubing to a balloon inflation port at the proximal end of the catheter tubing.

4. The multi-sensor catheter of claim 1, further comprising a guidewire lumen.

5. The multi-sensor catheter of claim 1, further comprising:
 a guidewire lumen;
 an inflatable balloon near the distal tip, the inflatable balloon being coupled by a balloon inflation lumen of the catheter tubing to a balloon inflation port at the proximal end of the catheter tubing; and
 wherein the catheter tubing has an outside diameter sized to allow insertion into the heart through a vein in an upper or lower arm.

6. A multi-sensor catheter for direct monitoring of blood pressure at first and second locations during cardiac catheterization, comprising:
 a length of catheter tubing comprising first and second lumens extending between a proximal end and a distal end comprising an atraumatic distal tip;
 first and second optical pressure sensors and first and second optical fibers, a sensor end of each optical fiber being attached and optically coupled to an individual one of the optical pressure sensors;
 the first and second optical fibers being inserted respectively into the first and second lumens of the catheter tubing, the sensor ends of each optical fiber being spaced apart lengthwise to provide a sensor arrangement with said first and second optical pressure sensors positioned at respective first and second sensor locations within a distal end portion of the catheter tubing;

a proximal end of each of the first and second optical fibers being coupled to an optical input/output connector at the proximal end of the catheter for connection to an optical control system;

an aperture in the catheter tubing adjacent each optical pressure sensor for fluid contact;

wherein said first and second sensor locations are spaced apart lengthwise to enable positioning of the first and second optical pressure sensors at first and second positions within one of: two chambers of the heart: a chamber of the heart and aorta; and a chamber of the heart and pulmonary artery; to provide concurrent blood pressure measurements by said first and second optical pressure sensors as positioned during cardiac catheterization.

7. The multi-sensor catheter of claim 6, wherein said first and second positions are one of:
a) right atrium and pulmonary artery;
b) right atrium and right ventricle;
c) left ventricle and left atrium;
d) right atrium and left atrium;
e) aorta and left ventricle; and
f) right ventricle and pulmonary artery.

\* \* \* \* \*

UNITED STATES PATENT AND TRADEMARK OFFICE
CERTIFICATE OF CORRECTION

| | | |
|---|---|---|
| PATENT NO. | : 11,197,619 B2 | |
| APPLICATION NO. | : 16/587659 | |
| DATED | : December 14, 2021 | |
| INVENTOR(S) | : Glover et al. | |

It is certified that error appears in the above-identified patent and that said Letters Patent is hereby corrected as shown below:

On the Title Page

Below item (72) Inventors, insert the following:
--(73) Assignee, HemoCath Ltd., Toronto (CA)--.

Signed and Sealed this
Fifth Day of July, 2022

Katherine Kelly Vidal
*Director of the United States Patent and Trademark Office*